US007718618B2

(12) United States Patent
Gallo et al.

(10) Patent No.: US 7,718,618 B2
(45) Date of Patent: May 18, 2010

(54) HUMAN CATHELICIDIN ANTIMICROBIAL PEPTIDES

(75) Inventors: Richard L. Gallo, San Diego, CA (US); Masamoto Murakami, Hokkaido (JP); Donald Y.M. Leung, Denver, CO (US)

(73) Assignees: The Regents of the University of California, Oakland, CA (US); National Jewish Medical and Research Center, Denver, CO (US)

( * ) Notice: Subject to any disclaimer, the term of this patent is extended or adjusted under 35 U.S.C. 154(b) by 886 days.

(21) Appl. No.: 10/575,552

(22) PCT Filed: Oct. 20, 2004

(86) PCT No.: PCT/US2004/034948

§ 371 (c)(1),
(2), (4) Date: Aug. 29, 2006

(87) PCT Pub. No.: WO2005/040201

PCT Pub. Date: May 6, 2005

(65) Prior Publication Data

US 2007/0037744 A1      Feb. 15, 2007

Related U.S. Application Data

(60) Provisional application No. 60/512,953, filed on Oct. 21, 2003.

(51) Int. Cl.
*A61K 38/10* (2006.01)
*A61K 38/16* (2006.01)

(52) U.S. Cl. ........................... 514/13; 514/12; 530/324; 530/325; 530/326

(58) Field of Classification Search ........................ None
See application file for complete search history.

(56) References Cited

U.S. PATENT DOCUMENTS

| 4,482,680 | A | 11/1984 | Sheldon |
| 5,618,675 | A | 4/1997 | Larrick |
| 6,040,291 | A | 3/2000 | Hirata |
| 2003/0022829 | A1 | 1/2003 | Maury |

FOREIGN PATENT DOCUMENTS

| EP | 1 358 888 A1 | 11/2003 |
| WO | 96/08508 | 3/1996 |
| WO | WO 02/13857 | 2/2002 |
| WO | WO 02/060468 A2 | 8/2002 |
| WO | 2004/098536 | 11/2004 |
| WO | 2005/040192 | 5/2005 |
| WO | 2005/040201 | 5/2005 |

OTHER PUBLICATIONS

Braun et al. "Setting the stage for bench-to-bedside movment of anti-HIV RNA inhibitors-gene therapy for AIDS in macaques" Frontiers in Bioscience, vol. 11, pp. 838-851, Jan. 2006.*
Gait et al. "Progress in anti-HIV structure based drug design." TIBTECH, vol. 13. pp. 430-438, Oct. 1995.*
Field et al. 'Herpesvirus Latency and Therapy-From a veterinary persepective' Anitviral Research, vol. 71. pp. 127-133. 2007.*
Kleymann et al. 'Agents and strategies in development of improved management of herpes simiplex virus infection and disease.' Expert Opin. INvestig. Drugs. vol. 14(2), pp. 135-161. 2005.*
Gill et al. The role of Toll-Like Receptor Ligangds/Agonsit in Protection AGainst Genital HSV-2 Infection. American Joural of Reproductive Immunology. vol. 59, pp. 35-43. 2008.*
CDC Fact Sheet: Genital HPV. pp. 1-2, Dec. 2007.*
Bowman, et al. "Prepro-Fall-99" Jun. 6, 1996, Database: A.sub.—Geneseq.sub.—21, Accession No. AAR92924, alignment result 4.
Johansson, J.; G. H. Gudmundsson; M. E. Rottenberg; K. D. Berndt; and B. Agerberth; "Conformation-dependent Antibacterial Activity of the Naturally Occurring Human Peptide LL-37" The Journal of Biological Chemistry; Feb. 6, 1998; 273(6):3718-3724.
Benincasa, Monica et al., "In vitro and in vivo antimicrobial activity of two alpha-helical cathelicidin peptides and of their synthetic analogs," Peptides, vol. 24, No. 11, pp. 1723-1731, Nov. 2003.
Brasel, Kenneth et al., Hematologic Effects on flt3 Ligand in Vivo in Mice, Blood, vol. 88, No. 6, pp. 2004-2012, 1996.
Clinical and Experimental Dermatology vol. 21, No. 3, pp. 185, May 1996.
Gallo, Richard L. et al., "Identification of CRAMP, a cathelin-related antimicriobial peptide expressed in the embryonic and adult mouse," J. Biol. Chem., vol. 272, No. 20, pp. 13088-13093, May 16, 1997.
Gennaro, Renato et al., "Pro-rich antimicrobial peptides from animals: structure, biological functions and mechanism of action," Current Pharmaceutical Design. vol. 8, No. 9, pp. 763-778, 2002.
Gennaro Renato et al., "Structural features and biological activities of the cathelicidin-derived antimicrobial peptides," Biopolymers, vol. 55, No. 1, pp. 31-49, 2000.
Gennaro, Renato et al., "Biological characterization of a novel mammalian antimicrobial peptide," Biochimica et Biophysica Acta, vol. 1425, No. 2, pp. 361-368, Oct. 23, 1998.
Ha, Jong-Myung et al., "Synthesis and Antibiotic Activities of CRAMP, a Cathelin-related Antimicrobial Peptide and Its Fragments," Bull. Korean Chem. Soc., vol. 20, No. 9, pp. 1073-1077, 1999.
Howell, Michael D. et al., "Selective Killing of Vaccinia Virus by LL-37: Implications for Eczema Vaccinatum," Journal of Immunology, vol. 172, pp. 1763-1767, 2004.

(Continued)

*Primary Examiner*—Anish Gupta
(74) *Attorney, Agent, or Firm*—Joseph R. Baker, Jr.; Gavrilovich Dodd & Lindsey LLP

(57) ABSTRACT

Provided are peptide and peptide consensus sequences, which inhibit bacterial growth and/or viral growth and mimic the activity of LL-37, CRAMP, and/or FALL-39. The peptides are useful as antimicrobials, anti-inflammatories and antiviral agents.

14 Claims, 22 Drawing Sheets

OTHER PUBLICATIONS

Johnson, B.Connor, "Posttranslational Covalent Modification of Proteins," Academic Press, NY, pp. 1-12 1983.

Kaufman, Randal et al., "Synthesis, Processing, and Secretion of Recombinant Human Factor VIII Expressed in Mammalian Cells," Journal of Biological Chemistry vol. 263, No. 13, pp. 6352-6362, 1988.

Kaufman, Randal, "Selection and Coamplification of Heterologous Genes in Mammalian Cells" Methods In Enzymology, vol. 185 pp. 527-566, 1990.

McKinnon, P et al., "Expression, purification and characterization of secreted recombinant human insulin-like growth factor—I (IGF-I) and the potent variant des (1-3) IGF-I in Chinese hamster ovary cells" Journal Molecular Endocrinology 6, pp. 231-239, 1991.

Merrifield, R.B.. "Solid Phase Peptide Synthesis" Journal. Am. Chem. Soc., vol. 85, p. 2149, 1962.

Ong, Peck et al., "Endogenous Antimicrobial Peptides and Skin Infections in Atopic Dermatitis," New England Journal of Medicine, vol. 347, No. 15, pp. 1151-1160, Oct. 10, 2002.

Rattan, Suresh I. et al., "Protein Synthesis, Posttranslational Modifications, and Aging," Annals of the N.Y. Academy of Science, vol. 663, pp. 48-62 (1992).

Sanchez et al., "Overexpression and structural study of the cathelicidin motif of the protegrin-3 precursor," Biochemistry, vol. 41, No. 1, pp. 21-30, Jan. 8, 2002.

Scott, Jamie et al.,"Searching for Peptide Ligands with an Epitope Library," Science Voll. 249, pp. 386-390 (1990).

Seifter, Sam et al., "Analysis for Protein Modifications and Nonprotein Cofactors," Methods of Enzymology, vol. 182, pp. 626-646, 1990.

Skerlavaj, Barbara et al., "Structural and functional analysis of horse cathelicidin peptides," Antimicrobial Agents Chemotherapy., vol. 45, No. 3, pp. 715-722, Mar. 2001.

Smeianov, Vladimir et al. "Activity of cecropin P1 and FA-LL-37 Against urogenital microflora" Microbes and Infection, vol. 2, pp. 773-777, 2000.

Smith, George, et al., "Libraries of Peptides and Proteins Displayed on Filamentous Phage," Methods Enzymology, vol. 217, pp. 228-257, 1993.

Stewart, John, et al., "Solid Phase Peptides Synthesis," W.H. Freeman and Copmany, San Francisco, 1969, pp. 27-62.

Tjabringa, G. Sandra et al., "The Antimicrobial Peptide LL-37 Activates Innate Immunity at the Airway Epithelial Surface by Transactivation of the Epidermal Growth Factor Receptor," Journal of Immunology, vol. 171, pp. 6690-6696, 2003.

Urlaub, Gail et al., "Isolation of Chinese Hamster cell mutants deficient in dihydrofolate reductase activity," Proc Natl Acad Sci USA, vol. 77, pp. 4216-4220, 1980.

Wood, Clive et al.,"High Level Synthesis of Immunoglobulins In Chinese Hamster Ovary Cells," The Journal of Immunology, Vo. 145, pp. 3011-3016, 1990.

Zaiou, Mohamed et al., "Antimicrobial and Protease Inhibitory Functions of the Human Cathelicidin (hCAP18/LL-37) Prosequence," The Society for Investigative Dermatology, vol. 120, No. 5, pp. 810-816, May 2003.

Zanetti, Margherita et al., "Cathelicidin peptides as candidates for a novel class of antimicrobials," Current Pharmaceutical Design, vol. 8, No. 9, pp. 779-793, 2002.

Zanetti, Margherita et al., "Structure and biology of cathelicidins," Adv. Exp. Med. Biol., vol. 479, pp. 203-218, 2000.

Zanetti et al., "The cathelicidin family of antimicrobial peptide precursors: a component of the oxygen-independent defense mechanisms of neutrophils," Annals N.Y. Academy of Scieces, vol. 832, pp. 147-162, Dec. 15, 1997.

Zanetti et al. "Cathelicidin Peptides as Candidates for a Novel Class of Antimicrobials" Current Pharmaceutical Design, vol. 8, No. 9, pp. 779-793, 2002.

* cited by examiner

Staph aureus
32 uM LL-37
20% TSB
10% FCS
pH 7.4

Staph aureus
32 uM LL-37
20% TSB
150 mM NaCl
10% FCS

Staph aureus
20% TSB
NO NaCl
No FCS

- - - 0mM NaHCO3
—— 50mM NaHCO3

Staph aureus
pH 7.4
20% TSB
150 mM NaCl
10% FCS

Cramp at 16 uM
20% TSB
no NaCl or FCS
pH 7.4 e. coli inner membrane permeability
no NaCL, FCS
pH 7.4
data are OD 420 with antibiotic/no antibiotic

SEQUENCE LISTING

```
<160> NUMBER OF SEQ ID NOS: 34

<210> SEQ ID NO 1
<211> LENGTH: 11
<212> TYPE: PRT
<213> ORGANISM: Homo sapiens
<220> FEATURE:
<221> NAME/KEY: X
<222> LOCATION: (1)..(2)
<223> OTHER INFORMATION: K or R
<220> FEATURE:
<221> NAME/KEY: X
<222> LOCATION: (3)..(3)
<223> OTHER INFORMATION: I or K
<220> FEATURE:
<221> NAME/KEY: X
<222> LOCATION: (4)..(4)
<223> OTHER INFORMATION: V or G
<220> FEATURE:
<221> NAME/KEY: X
<222> LOCATION: (5)..(5)
<223> OTHER INFORMATION: Q or R
<220> FEATURE:
<221> NAME/KEY: X
<222> LOCATION: (6)..(6)
<223> OTHER INFORMATION: K or R
<220> FEATURE:
```

```
<221> NAME/KEY: X
<222> LOCATION: (7)..(7)
<223> OTHER INFORMATION: any amino acid
<220> FEATURE:
<221> NAME/KEY: X
<222> LOCATION: (8)..(8)
<223> OTHER INFORMATION: L or F
<220> FEATURE:
<221> NAME/KEY: X
<222> LOCATION: (9)..(11)
<223> OTHER INFORMATION: any amino acid

<400> SEQUENCE: 1

Xaa Xaa Xaa Xaa Xaa Xaa Xaa Xaa Xaa Xaa Xaa
1               5                   10

<210> SEQ ID NO 2
<211> LENGTH: 11
<212> TYPE: PRT
<213> ORGANISM: Homo sapiens

<400> SEQUENCE: 2

Lys Arg Ile Val Gln Arg Ile Lys Asp Val Phe
1               5                   10

<210> SEQ ID NO 3
<211> LENGTH: 8
<212> TYPE: PRT
<213> ORGANISM: Homo sapiens

<400> SEQUENCE: 3

Arg Lys Ser Lys Glu Lys Ile Gly
1               5

<210> SEQ ID NO 4
<211> LENGTH: 8
<212> TYPE: PRT
<213> ORGANISM: Homo sapiens

<400> SEQUENCE: 4

Lys Ser Lys Glu Lys Ile Gly Lys
1               5

<210> SEQ ID NO 5
<211> LENGTH: 739
<212> TYPE: DNA
<213> ORGANISM: Homo sapiens

<400> SEQUENCE: 5
taaagcaaac cccagcccac accctggcag gcagccaggg atgggtggat caggaaggct      60
cctggttggg cttttgcatc aggctcaggc tgggcataaa ggaggctcct gtgggctaga     120
gggaggcaga catggggacc atgaagaccc aaagggatgg ccactccctg ggcggtggt     180 cactggtgct cctgctgctg ggcctggtga tgcctctggc catcattgcc caggtcctca     240
gctacaagga agctgtgctt cgtgctatag atggcatcaa ccagcggtcc tcggatgcta     300
acctctaccg cctcctggac ctggacccca ggcccacgat ggatgggac ccagacacgc      360 caaagcctgt gagcttcaca gtgaaggaga cagtgtgccc caggacgaca cagcagtcac     420
cagaggattg tgacttcaag aaggacgggt ggtgaagcg gtgtatgggg acagtgaccc     480
tcaaccaggc caggggctcc tttgacatca gttgtgataa ggataacaag agatttgccc     540
tgctgggtga tttcttccgg aaatctaaag agaagattgg caaagagttt aaaagaattg     600
tccagagaat caaggatttt ttgcggaatc ttgtacccag gacagagtcc tagtgtgtgc     660
```

```
cctaccctgg ctcaggcttc tgggctctga gaaataaact atgagagcaa tttcaaaaaa      720
aaaaaaaaaa aaaaaaaaa                                                   739

<210> SEQ ID NO 6
<211> LENGTH: 170
<212> TYPE: PRT
<213> ORGANISM: Homo sapiens

<400> SEQUENCE: 6

Met Lys Thr Gln Arg Asn Gly His Ser Leu Gly Arg Trp Ser Leu Val
1               5                   10                  15

Leu Leu Leu Leu Gly Leu Val Met Pro Leu Ala Ile Ile Ala Gln Val
            20                  25                  30

Leu Ser Tyr Lys Glu Ala Val Leu Arg Ala Ile Asp Gly Ile Asn Gln
        35                  40                  45

Arg Ser Ser Asp Ala Asn Leu Tyr Arg Leu Leu Asp Leu Asp Pro Arg
    50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
    130                 135                 140

Lys Ile Gly Lys Glu Phe Lys Arg Ile Val Gln Arg Ile Asp Asp Phe
145                 150                 155                 160

Leu Arg Asn Leu Val Pro Arg Thr Glu Ser
                165                 170

<210> SEQ ID NO 7
<211> LENGTH: 519
<212> TYPE: DNA
<213> ORGANISM: Homo sapiens

<400> SEQUENCE: 7
atgcagttcc agagggacgt cccctccctg tggctgtggc ggtcactatc actgctgctg       60
ctactgggcc tggggttctc ccagaccccc agctacaggg atgctgtgct ccagctgtg      120 gatgacttca ccagcagtc cctagacacc aatctctacc gtctcctgga cctggatcct      180
gagccccaag gggacgagga tccagatact cccaagtctg tgaggttccg agtgaaggag      240
actgtatgtg gcaaggcaga gcggcagcta cctgagcaat gtgccttcaa ggaacagggg      300
gtggtgaagc agtgtatggg ggcagtcacc ctgaacccgg ccgctgattc ttttgacatc      360
agctgtaacg agcctggtgc acagcccttt cggttcaaga aaatttcccg gctggctgga      420
cttctccgca aggtgggga agagattggt gaaaagctta agaaaattgg ccagaaaatt      480
aagaattttt ttcagaaact tgtccctcag ccagagtag                            519

<210> SEQ ID NO 8
<211> LENGTH: 173
<212> TYPE: PRT
<213> ORGANISM: murine

<400> SEQUENCE: 8
```

```
Met Gln Phe Gln Arg Asp Val Pro Ser Leu Trp Leu Trp Arg Ser Leu
1               5                  10                  15

Ser Leu Leu Leu Leu Gly Leu Gly Phe Ser Gln Thr Pro Ser Tyr
            20                  25                  30

Arg Asp Ala Val Leu Arg Ala Val Asp Phe Asn Gln Gln Ser Leu
            35                  40                  45

Asp Thr Asn Leu Tyr Arg Leu Leu Asp Leu Asp Pro Glu Pro Gln Gly
        50                  55                  60

Asp Glu Asp Pro Asp Thr Pro Lys Ser Val Arg Phe Arg Val Lys Glu
65                  70                  75                  80

Thr Val Cys Gly Lys Ala Glu Arg Gln Leu Pro Glu Gln Cys Ala Phe
            85                  90                  95

Lys Glu Gln Gly Val Val Lys Gln Cys Met Gly Ala Val Thr Leu Asn
                100                 105                 110

Pro Ala Ala Asp Ser Phe Asp Ile Ser Cys Asn Glu Pro Gly Ala Gln
            115                 120                 125

Pro Phe Arg Phe Lys Lys Ile Ser Arg Leu Ala Gly Leu Leu Arg Lys
        130                 135                 140

Gly Gly Glu Lys Ile Gly Glu Lys Leu Lys Lys Ile Gly Gln Lys Ile
145                 150                 155                 160

Lys Asn Phe Phe Gln Lys Leu Val Pro Gln Pro Glu Gln
                165                 170

<210> SEQ ID NO 9
<211> LENGTH: 172
<212> TYPE: PRT
<213> ORGANISM: canine

<400> SEQUENCE: 9

Met Glu Thr Gln Lys Asp Ser Pro Ser Leu Gly Arg Trp Ser Leu Leu
1               5                  10                  15

Leu Leu Leu Leu Gly Leu Val Ile Thr Pro Ala Ala Ser Arg Ala Leu
            20                  25                  30

Ser Tyr Arg Glu Ala Val Leu Arg Ala Val Asn Gly Phe Asn Gln Arg
            35                  40                  45

Ser Ser Glu Glu Asn Leu Tyr Arg Leu Leu Gln Leu Asn Ser Gln Pro
        50                  55                  60

Lys Gly Asp Glu Asp Pro Asn Ile Pro Lys Pro Val Ser Phe Thr Val
65                  70                  75                  80

Lys Glu Thr Val Cys Pro Lys Thr Thr Gln Gln Pro Leu Glu Gln Cys
            85                  90                  95

Gly Phe Lys Asp Asn Gly Leu Val Lys Gln Cys Glu Gly Thr Val Ile
                100                 105                 110

Leu Asp Glu Asp Thr Gly Tyr Phe Asp Leu Asn Cys Asp Ser Ile Leu
            115                 120                 125

Gln Val Lys Lys Ile Asp Arg Leu Lys Glu Leu Ile Thr Thr Gly Ala
        130                 135                 140

Gln Lys Ile Gly Lys Lys Ile Arg Arg Ile Gly Gln Arg Ile Lys Asp
145                 150                 155                 160

Phe Leu Lys Asn Leu Gln Pro Arg Glu Glu Lys Ser
                165                 170

<210> SEQ ID NO 10
<211> LENGTH: 172
<212> TYPE: PRT
```

```
<213> ORGANISM: porcine

<400> SEQUENCE: 10

Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asn Pro Ser Ile His Ser Leu Asp Ile Ser Cys Asn Glu Ile Gln
        115                 120                 125

Ser Val Arg Arg Arg Pro Arg Pro Tyr Leu Pro Arg Pro Arg Pro
    130                 135                 140

Pro Pro Phe Phe Pro Pro Arg Leu Pro Pro Arg Ile Pro Pro Gly Phe
145                 150                 155                 160

Pro Pro Arg Phe Pro Pro Arg Phe Pro Gly Lys Arg
                165                 170

<210> SEQ ID NO 11
<211> LENGTH: 176
<212> TYPE: PRT
<213> ORGANISM: goat

<400> SEQUENCE: 11

Met Glu Thr Gln Gly Ala Ser Leu Ser Leu Gly Arg Trp Ser Leu Trp
1               5                   10                  15

Leu Leu Leu Leu Gly Leu Val Val Pro Leu Ala Ser Ala Gln Ala Leu
            20                  25                  30

Ser Tyr Arg Glu Ala Val Leu Arg Ala Val Gly Gln Leu Asn Glu Arg
        35                  40                  45

Ser Ser Glu Ala Asn Leu Tyr Arg Leu Leu Glu Leu Asp Pro Ala Pro
    50                  55                  60

Asn Asp Glu Val Asp Pro Gly Thr Arg Lys Pro Val Ser Phe Thr Val
65                  70                  75                  80

Lys Glu Thr Val Cys Pro Arg Thr Thr Gln Gln Pro Pro Glu Glu Cys
                85                  90                  95

Asp Phe Lys Glu Asn Gly Leu Val Lys Gln Cys Val Gly Thr Val Thr
            100                 105                 110

Leu Asp Pro Ser Asn Asp Gln Phe Asp Ile Asn Cys Asn Glu Leu Gln
        115                 120                 125

Ser Val Arg Phe Arg Pro Pro Ile Arg Arg Pro Pro Ile Arg Pro Pro
    130                 135                 140

Phe Asn Pro Pro Phe Arg Pro Pro Val Arg Pro Pro Phe Arg Pro Pro
145                 150                 155                 160

Phe Arg Pro Pro Phe Arg Pro Pro Ile Gly Pro Phe Pro Gly Arg Arg
                165                 170                 175
```

```
<210> SEQ ID NO 12
<211> LENGTH: 5
<212> TYPE: PRT
<213> ORGANISM: Unknown
<220> FEATURE:
<223> OTHER INFORMATION: linker moity

<400> SEQUENCE: 12

Gly Gly Gly Gly Ser
1               5

<210> SEQ ID NO 13
<211> LENGTH: 16
<212> TYPE: PRT
<213> ORGANISM: Homo sapiens

<400> SEQUENCE: 13

Lys Arg Ile Val Gln Arg Ile Lys Asp Phe Leu Arg Asn Leu Val Pro
1               5                   10                  15

<210> SEQ ID NO 14
<211> LENGTH: 17
<212> TYPE: PRT
<213> ORGANISM: Homo sapiens

<400> SEQUENCE: 14

Lys Arg Ile Val Gln Arg Ile Lys Asp Phe Leu Arg Asn Leu Val Pro
1               5                   10                  15

Arg

<210> SEQ ID NO 15
<211> LENGTH: 18
<212> TYPE: PRT
<213> ORGANISM: Homo sapiens

<400> SEQUENCE: 15

Lys Arg Ile Val Gln Arg Ile Lys Asp Phe Leu Arg Asn Leu Val Pro
1               5                   10                  15

Arg Thr

<210> SEQ ID NO 16
<211> LENGTH: 19
<212> TYPE: PRT
<213> ORGANISM: Homo sapiens

<400> SEQUENCE: 16

Lys Arg Ile Val Gln Arg Ile Lys Asp Phe Leu Arg Asn Leu Val Pro
1               5                   10                  15

Arg Thr Glu

<210> SEQ ID NO 17
<211> LENGTH: 20
<212> TYPE: PRT
<213> ORGANISM: Homo sapiens

<400> SEQUENCE: 17

Lys Arg Ile Val Gln Arg Ile Lys Asp Phe Leu Arg Asn Leu Val Pro
1               5                   10                  15

Arg Thr Glu Ser
            20

<210> SEQ ID NO 18
<211> LENGTH: 26
```

```
<212> TYPE: PRT
<213> ORGANISM: Homo sapiens

<400> SEQUENCE: 18

Lys Ser Lys Glu Lys Ile Gly Lys Glu Phe Lys Arg Ile Val Gln Arg
1               5                   10                  15

Ile Lys Asp Phe Leu Arg Asn Leu Val Pro
            20                  25

<210> SEQ ID NO 19
<211> LENGTH: 27
<212> TYPE: PRT
<213> ORGANISM: Homo sapiens

<400> SEQUENCE: 19

Lys Ser Lys Glu Lys Ile Gly Lys Glu Phe Lys Arg Ile Val Gln Arg
1               5                   10                  15

Ile Lys Asp Phe Leu Arg Asn Leu Val Pro Arg
            20                  25

<210> SEQ ID NO 20
<211> LENGTH: 28
<212> TYPE: PRT
<213> ORGANISM: Homo sapiens

<400> SEQUENCE: 20

Lys Ser Lys Glu Lys Ile Gly Lys Glu Phe Lys Arg Ile Val Gln Arg
1               5                   10                  15

Ile Lys Asp Phe Leu Arg Asn Leu Val Pro Arg Thr
            20                  25

<210> SEQ ID NO 21
<211> LENGTH: 29
<212> TYPE: PRT
<213> ORGANISM: Homo sapiens

<400> SEQUENCE: 21

Lys Ser Lys Glu Lys Ile Gly Lys Glu Phe Lys Arg Ile Val Gln Arg
1               5                   10                  15

Ile Lys Asp Phe Leu Arg Asn Leu Val Pro Arg Thr Glu
            20                  25

<210> SEQ ID NO 22
<211> LENGTH: 30
<212> TYPE: PRT
<213> ORGANISM: Homo sapiens

<400> SEQUENCE: 22

Lys Ser Lys Glu Lys Ile Gly Lys Glu Phe Lys Arg Ile Val Gln Arg
1               5                   10                  15

Ile Lys Asp Phe Leu Arg Asn Leu Val Pro Arg Thr Glu Ser
            20                  25                  30

<210> SEQ ID NO 23
<211> LENGTH: 27
<212> TYPE: PRT
<213> ORGANISM: Homo sapiens

<400> SEQUENCE: 23

Arg Lys Ser Lys Glu Lys Ile Gly Lys Glu Phe Lys Arg Ile Val Gln
1               5                   10                  15

Arg Ile Lys Asp Phe Leu Arg Asn Leu Val Pro
            20                  25
```

-continued

```
                20                  25

<210> SEQ ID NO 24
<211> LENGTH: 28
<212> TYPE: PRT
<213> ORGANISM: Homo sapiens

<400> SEQUENCE: 24

Arg Lys Ser Lys Glu Lys Ile Gly Lys Glu Phe Lys Arg Ile Val Gln
1               5                   10                  15

Arg Ile Lys Asp Phe Leu Arg Asn Leu Val Pro Arg
            20                  25

<210> SEQ ID NO 25
<211> LENGTH: 29
<212> TYPE: PRT
<213> ORGANISM: Homo sapiens

<400> SEQUENCE: 25

Arg Lys Ser Lys Glu Lys Ile Gly Lys Glu Phe Lys Arg Ile Val Gln
1               5                   10                  15

Arg Ile Lys Asp Phe Leu Arg Asn Leu Val Pro Arg Thr
            20                  25

<210> SEQ ID NO 26
<211> LENGTH: 30
<212> TYPE: PRT
<213> ORGANISM: Homo sapiens

<400> SEQUENCE: 26

Arg Lys Ser Lys Glu Lys Ile Gly Lys Glu Phe Lys Arg Ile Val Gln
1               5                   10                  15

Arg Ile Lys Asp Phe Leu Arg Asn Leu Val Pro Arg Thr Glu
            20                  25                  30

<210> SEQ ID NO 27
<211> LENGTH: 31
<212> TYPE: PRT
<213> ORGANISM: Homo sapiens

<400> SEQUENCE: 27

Arg Lys Ser Lys Glu Lys Ile Gly Lys Glu Phe Lys Arg Ile Val Gln
1               5                   10                  15

Arg Ile Lys Asp Phe Leu Arg Asn Leu Val Pro Arg Thr Glu Ser
            20                  25                  30

<210> SEQ ID NO 28
<211> LENGTH: 36
<212> TYPE: PRT
<213> ORGANISM: Homo sapiens

<400> SEQUENCE: 28

Leu Gly Asp Phe Phe Arg Lys Ser Lys Glu Lys Ile Gly Lys Glu Phe
1               5                   10                  15

Lys Arg Ile Val Gln Arg Ile Lys Asp Phe Leu Arg Asn Leu Val Pro
            20                  25                  30

Arg Thr Glu Ser
        35

<210> SEQ ID NO 29
<211> LENGTH: 22
<212> TYPE: PRT
```

```
<213> ORGANISM: Unknown
<220> FEATURE:
<223> OTHER INFORMATION: linker moiety

<400> SEQUENCE: 29

Gly Gly Gly Gly Gly Gly Ser Met Phe Gly Gly Ala Lys Lys Arg Ser
1               5                   10                  15

Gly Gly Gly Gly Gly Gly
            20

<210> SEQ ID NO 30
<211> LENGTH: 11
<212> TYPE: PRT
<213> ORGANISM: Homo sapiens

<400> SEQUENCE: 30

Ser Ser Leu Leu Glu Lys Gly Leu Asp Gly Ala
1               5                   10

<210> SEQ ID NO 31
<211> LENGTH: 5
<212> TYPE: PRT
<213> ORGANISM: Homo sapiens

<400> SEQUENCE: 31

Ser Ser Leu Leu Glu
1               5

<210> SEQ ID NO 32
<211> LENGTH: 37
<212> TYPE: PRT
<213> ORGANISM: Homo sapiens

<400> SEQUENCE: 32

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 33
<211> LENGTH: 47
<212> TYPE: PRT
<213> ORGANISM: Homo sapiens

<400> SEQUENCE: 33

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val
        35                  40                  45

<210> SEQ ID NO 34
<211> LENGTH: 129
<212> TYPE: PRT
<213> ORGANISM: Unknown
<220> FEATURE:
<223> OTHER INFORMATION: concensus amino acid sequence

<400> SEQUENCE: 34

Met Glu Thr Gln Arg Ser Ser Leu Gly Arg Trp Ser Leu Leu Leu Leu
```

-continued

| | | | | | | | | | | | | | | | |
|---|---|---|---|---|---|---|---|---|---|---|---|---|---|---|---|
| 1 | | | | 5 | | | | | 10 | | | | | 15 | |
| Leu | Gly | Leu | Val | Pro | Ala | Ile | Ala | Gln | Ala | Leu | Ser | Tyr | Arg | Glu | Ala |
| | | | 20 | | | | | 25 | | | | | 30 | | |
| Val | Leu | Arg | Ala | Val | Asp | Asn | Gln | Arg | Ser | Ser | Glu | Ala | Asn | Leu | Tyr |
| | | 35 | | | | | 40 | | | | | 45 | | | |
| Arg | Leu | Leu | Leu | Asp | Pro | Pro | Asp | Glu | Asp | Pro | Thr | Pro | Lys | Pro | Val |
| | 50 | | | | | 55 | | | | | 60 | | | | |
| Ser | Phe | Thr | Val | Lys | Glu | Thr | Val | Cys | Pro | Arg | Thr | Thr | Gln | Gln | Pro |
| 65 | | | | | 70 | | | | | 75 | | | | | 80 |
| Pro | Glu | Cys | Asp | Phe | Lys | Glu | Asn | Gly | Leu | Val | Lys | Gln | Cys | Gly | Thr |
| | | | | 85 | | | | | 90 | | | | | 95 | |
| Val | Thr | Leu | Asn | Pro | Ser | Phe | Asp | Ile | Ser | Cys | Asn | Glu | Pro | Gly | Gln |
| | | | 100 | | | | | 105 | | | | | 110 | | |
| Val | Arg | Arg | Lys | Ile | Gly | Arg | Ile | Gln | Arg | Ile | Lys | Phe | Leu | Pro | Arg |
| | | 115 | | | | | 120 | | | | | 125 | | | |
| Arg | | | | | | | | | | | | | | | |

HUMAN CATHELICIDIN ANTIMICROBIAL PEPTIDES

CROSS REFERENCE TO RELATED APPLICATIONS

This application is filed under §371 and claims priority to International Application No. PCT/US2004/034948, which application claims priority under 35 U.S.C. §119 from Provisional Application Ser. No. 60/512,953, filed Oct. 21, 2003, the disclosures of which are incorporated herein by reference.

STATEMENT AS TO FEDERALLY SPONSORED RESEARCH

The U.S. Government has certain rights in this disclosure pursuant to Grant Nos. AR41256 and AI052453 awarded by the National Institutes of Health.

TECHNICAL FIELD

The disclosure relates peptides and methods to treat viral and other microbial infections.

BACKGROUND

Small, cationic antimicrobial peptides (AMPs) are naturally occurring antibiotics of the innate immune system. AMPs are widely distributed in animals and plants and are among the most ancient host defense factors. Their spectrum of activity includes Gram-positive and Gram-negative bacteria as well as fungi and certain viruses. As resistance of pathogenic microbes to conventional antibiotics increases, researchers are exploring these endogenous antibiotics as a potential source or new therapies against variety of infectious diseases.

Virus infections occur following entrance of virions into host cells by a variety of mechanisms including endocytosis of non-enveloped viruses and fusion with the cell membrane by enveloped viruses. One primary barrier to the infection is epithelial keratinocyte of the skin. Alterations in skin barrier function are seen in atopic dermatitis (AD). This finding may contribute to infection with bacteria and selected viruses, including Herpesviridae (herpes simplex virus (HSV), varicella-zoster virus) and vaccinia virus. However, it is unlikely that a defect in the physical barrier alone accounts for the remarkably increased susceptibility of AD patients to recurrent skin infections. Patients with plaque psoriasis, a common Th1-mediated inflammatory skin disease also associated with skin barrier dysfunction, do not have increased susceptibility to microbial skin infection.

SUMMARY

The invention provides a method for inhibiting the spread and/or reducing the risk of infection of a virus comprising contacting a virus with an inhibiting effective amount of a cathelicidin functional fragment. In one aspect the cathelicidin functional fragment comprises a peptide that is 16-36 amino acids in length; and contains the sequence $NH_2$—$X_1X_2X_3X_4X_5X_6IKX_7FX_8X_9X_{10}LX_{11}P$—COOH (SEQ ID NO: 1), wherein $X_1$, $X_2$, and $X_6$ are individually K or R; wherein $X_3$ is I or K; wherein $X_4$ is V or G; wherein $X_5$ is Q or R; wherein $X_7$, $X_9$, $X_{10}$, and $X_{11}$ are each individually any amino acid; and wherein $X_8$ is L or F. In a further aspect, the peptide is about 16 to 20 amino acids in length and is selected from the group consisting of (a) $NH_2$-KRIVQRIKDFLRNLVP—COOH (SEQ ID NO:13); (b) $NH_2$-KRIVQRIKDFLRNLVPR—COOH (SEQ ID NO:14); (c) $NH_2$-KRIVQRIKDFLRNLVPRT-COOH (SEQ ID NO:15); (d) $NH_2$-KRIVQRIKDFLRNLVPRTE-COOH (SEQ ID NO:16); and (e) $NH_2$-KRIVQRIKDFLRNLVPRTES-COOH (SEQ ID NO:17). In yet a further aspect the peptide is about 26 to 30 amino acids in length and is selected from the group consisting of (a) $NH_2$-KSKEKIGKEFKRIVQRIKDFLRNLVP—COOH (SEQ ID NO:18); (b) $NH_2$-KSKEKIGKEFKRIVQRIKDFLRNLVPR—COOH (SEQ ID NO:19); (c) $NH_2$-KSKEKIGKEFKRIVQRIKDFLRNLVPRT-COOH (SEQ ID NO:20); (d) $NH_2$-KSKEKIGKEFKRIVQRIKDFLRNLVPRTE-COOH (SEQ ID NO:21); and (e) $NH_2$-KSKEKIGKEFKRIVQRIKDFLRNLVPRTES-COOH (SEQ ID NO:22). In another embodiment the peptide is about 27 to 31 amino acids in length and is selected from the group consisting of (a) $NH_2$-RKSKEKIGKEFKRIVQRIKDFLRNLVP—COOH (SEQ ID NO:23); (b) $NH_2$-RKSKEKIGKEFKRIVQRIKDFLRNLVPR—COOH (SEQ ID NO:24); (c) $NH_2$-RKSKEKIGKEFKRIVQRIKDFLRNLVPRT-COOH (SEQ ID NO:25); (d) $NH_2$-RKSKEKIGKEFKRIVQRIKDFLRNLVPRTE-COOH (SEQ ID NO:26); (e) $NH_2$-RKSKEKIGKEFKRIVQRIKDFLRNLVPRTES-COOH (SEQ ID NO:27). In a specific embodiment, the peptide is 36 amino acids in length and consists of the sequence $NH_2$-LGDFFRKSKEKIGKEFKRIVQRIKDFLRNLVPRTES-COOH (SEQ ID NO:28).

The invention also provides a method of treating atopic dermatitis comprising contacting a subject having or suspected of having atopic dermatitis with an inhibiting effective amount of a cathelicidin functional fragment.

The details of one or more embodiments of the invention are set forth in the accompanying drawings and the description below. Other features, objects, and advantages of the invention will be apparent from the description and drawings, and from the claims.

SSLLE (SEQ ID NO:31), (2): LL-37 identified by mass spectrometry (MW 4493) and immunoblot. Data representative of single experiment repeated 5 times with separate sweat preparations.

Figure 11:
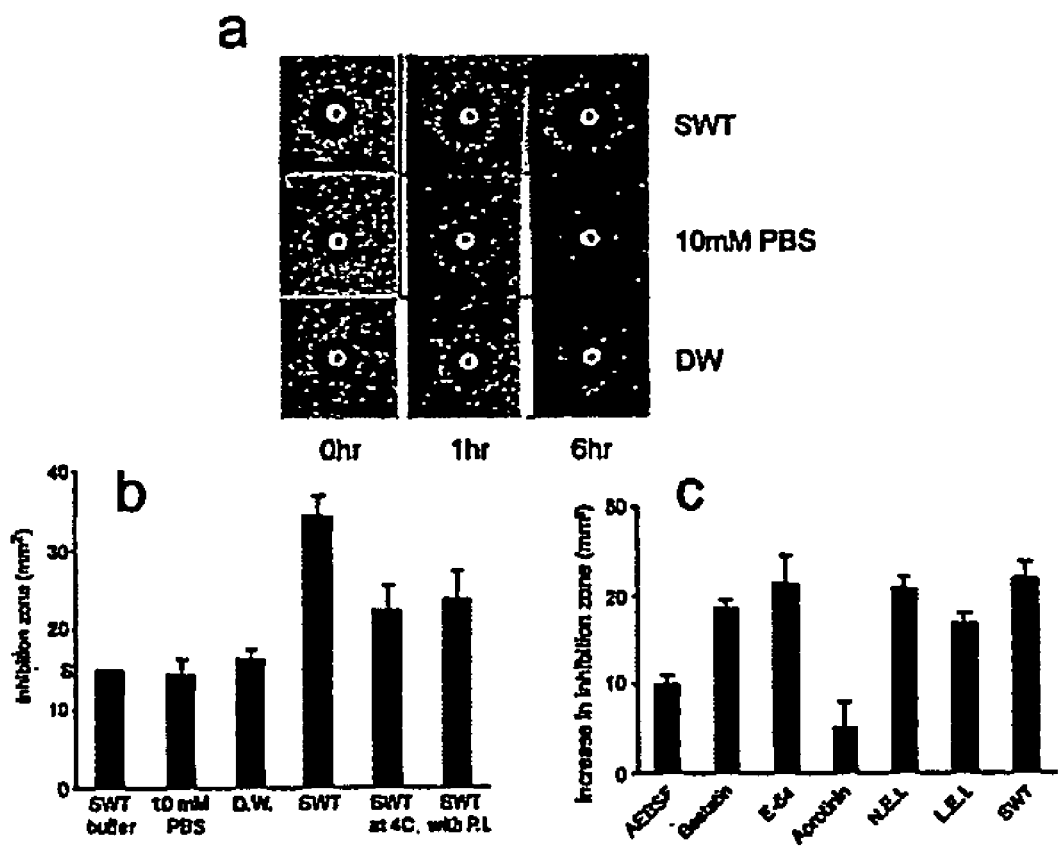

FIG. 11A-C shows serine protease in sweat enhances cathelicidin antimicrobial activity. Antibacterial activity evaluated by radial diffusion assay against *S. aureus* mprF after incubation of LL-37 (32 uM) in sweat. a) Increase in the inhibition zone is seen when incubated in sweat but not 10 mM PBS or distilled water (DW). b) Diameters of inhibition zone after 6 hr incubation at 37° C. in (SWT buffer; sweat buffer salts alone), (PBS), (D.W.; distilled water), (SWT; sterile filtered human sweat at 37° C.), (SWT at 4° C.), (SWT with PI, with protease inhibitor cocktail). c) Action of specific protease inhibitors on gain of antimicrobial activity. Data show increase in inhibition zone at 37° C. after 6 hr compared to 0 hr. Serine protease inhibitors AEBSF and Aprotinin were most effective. N.E.I.=neutrophil elastase inhibitor, L.E.I.=leukocyte elastase inhibitor. Data are triplicate determinations±SEM from single experiment representative of 3.

Figure 12:
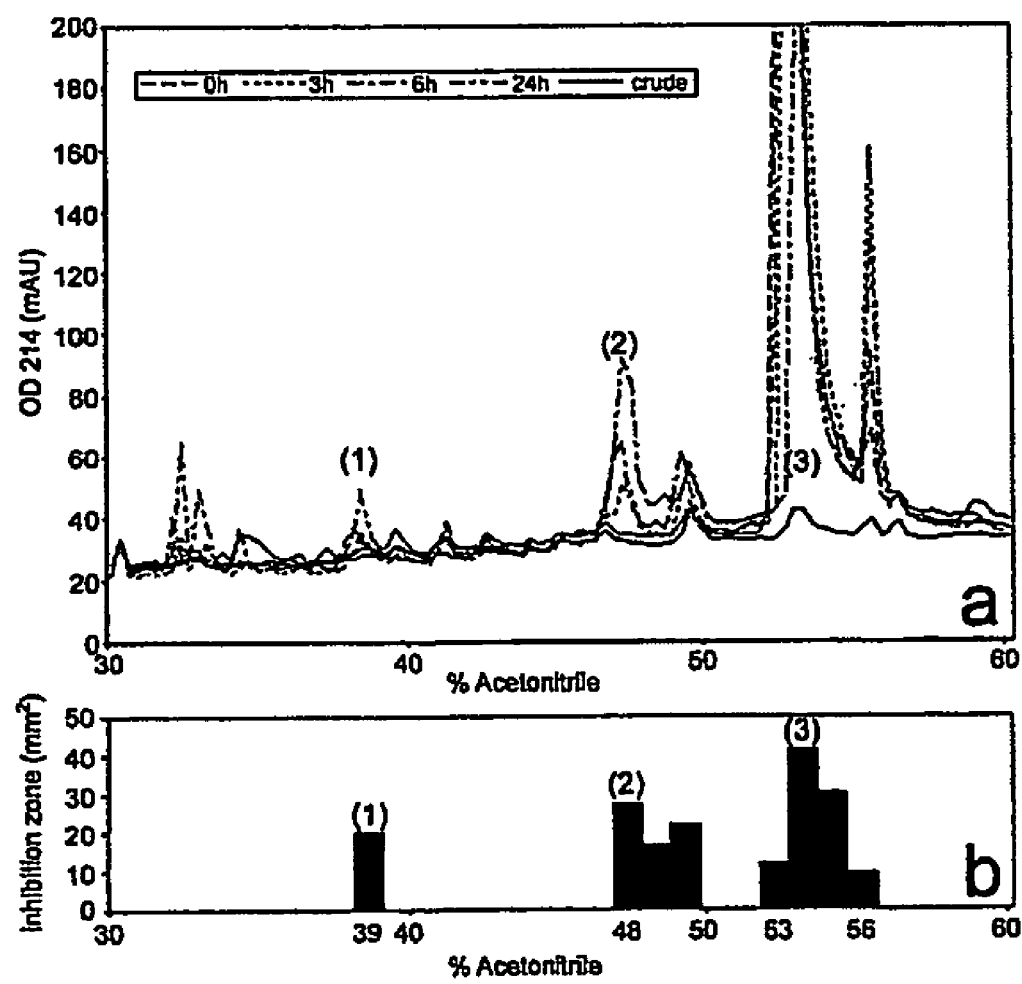

FIG. 12A-B shows purification of novel cathelicidin peptides generated from LL-37 a) Human sweat was separated by HPLC on C18. Absorbance profile at 214 nm is shown for eluted material from 30% to 60% acetonitrile. Crude is sweat prior to addition of LL-37, overlay plots show separate runs of sweat following addition of 32 nmoles of LL-37 and incubation for 0 to 24 hr at 37° C. b) Antibacterial activity with radial diffusion assay against *S. aureus* mprF of fractions eluted from 24 hr sample in a. Peaks with antimicrobial activity are labeled 1 and 2 and 3.

Figure 3:
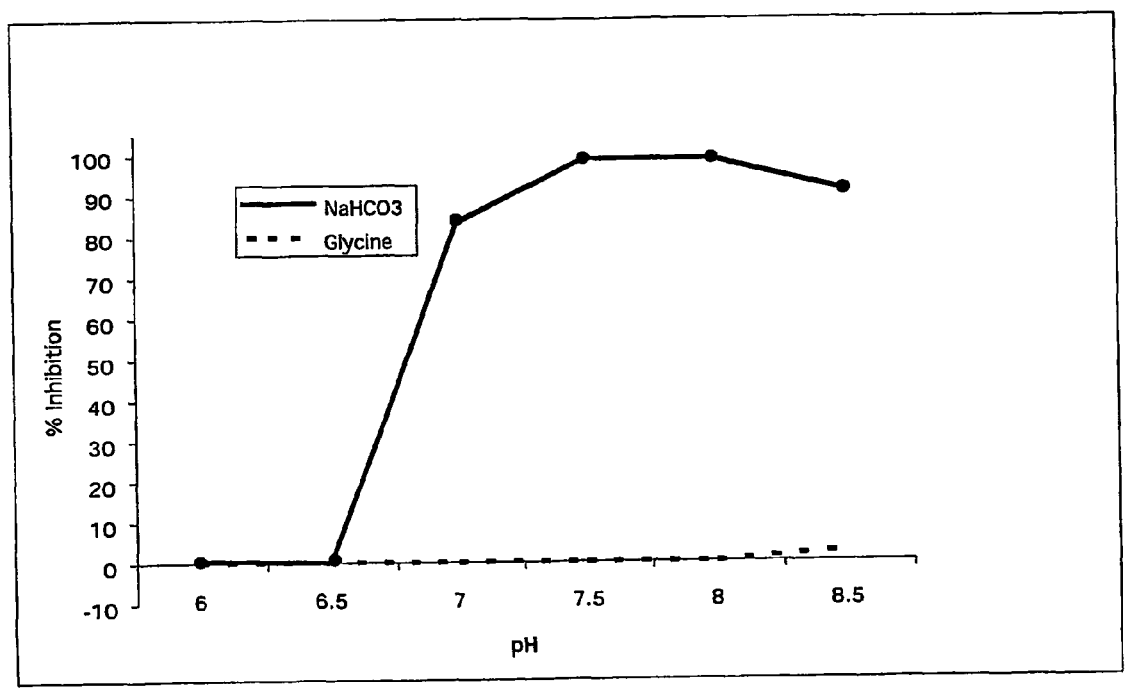
FIG. 3 shows that bicarbonate itself, not pH, is responsible for antimicrobial enhancement. Inhibition of *S. aureus* was measured in 20% TSB, 10% FBS 1 mM $NaH_2PO_4$, 150 mM NaCl, with either 50 mM $NaHCO_3$ or SOMM Glycine buffer at various pH. Only bicarbonate containing media was able to confer increased antimicrobial activity to LL-37.
Figure 4:
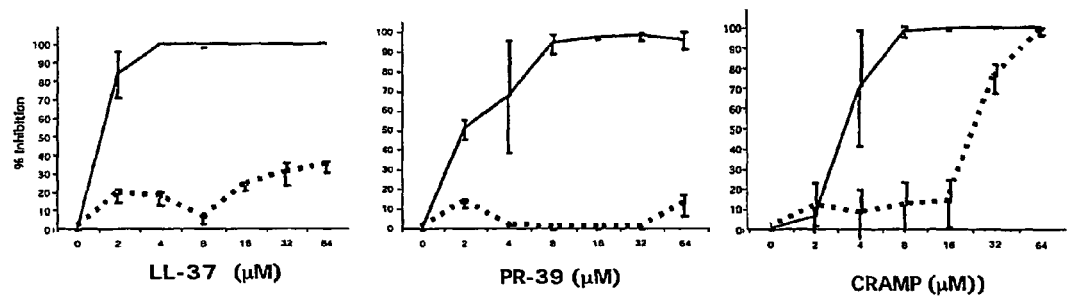
FIG. 4 shows that bicarbonate enhances activity of cathelicidin antimicrobial peptides. Inhibition of *Staph aureus* growth in the presence of various concentrations of human (LL-37), murine (CRAMP) and porcine (PR-39). Cathelicidin antimicrobial peptides was measured in 20% TSB, 1 mM $NaH_2PO_4$, with, or without, SOMM $NaHCO_3$ at pH 7.4. The presence of $NaHCO_3$ greatly reduced the minimal inhibitory concentration (MIC) of all three peptides.
Figure 5:
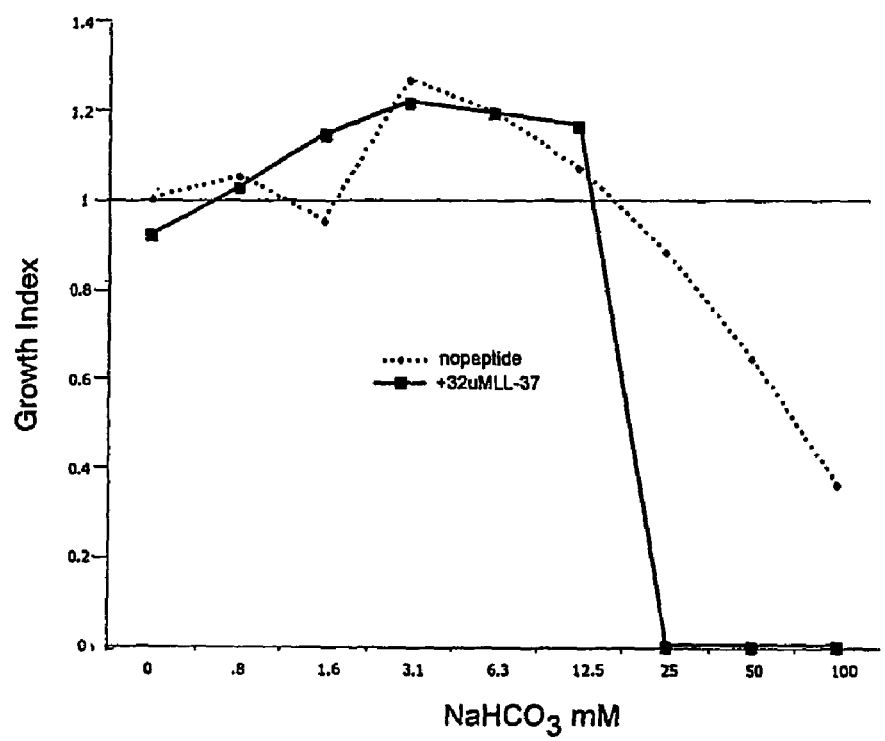
FIG. 5 demonstrates that 25 mM $NaHCO_3$ enhances LL-37 activity without effecting bacterial growth. The growth of *S. aureus* in the presence, or absence, of 32 µM LL-37 was measured in 20% TSB, 10% FBS, 1 mM $NaH_2PO_4$, 150 mM NaCl, and various concentrations of $NaHCO_3$, all at pH 7.4. 25 mM $NaHCO_3$ yielded complete inhibition of bacterial growth in the presence of LL-37, but not without peptide. High concentrations of $NaHCO_3$ retarded the growth of *S. aureus*.
Figure 6:
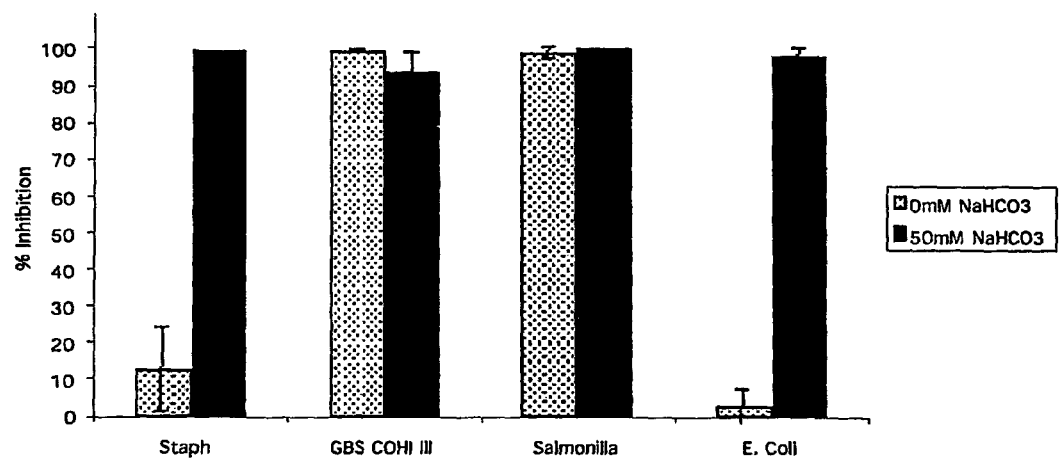
FIG. 6 shows that $NaHCO_3$ enhances antimicrobial activity against gram negative and positive bacteria. *S. aureus* and *E. coli* were resistant to 16 µM CRAMP without SOM $NaHCO_3$, but became susceptible in its presence in 20% TSB, 1 mM $NaH_2PO_4$ at pH 7.4. Group B Strep (GBS) and *Salmonella* were susceptible even without $NaHCO_3$.
Figure 7:
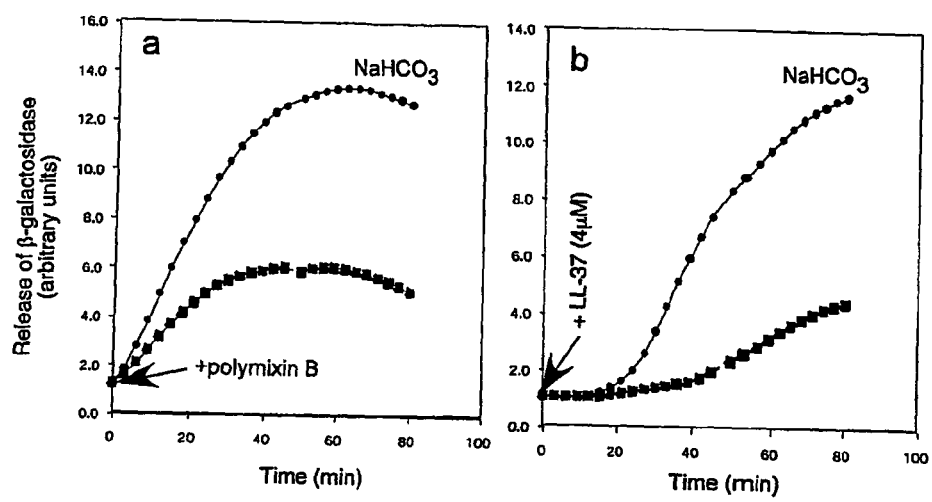
FIG. 7 demonstrates that $NaHCO_3$ enables direct membrane disruptlion of *S. aureus*. Release of cytoplasmic expressed beta-galactosidase was measure from bacteria with and without the addition of $NaHCO_3$. (A) Polymyxin B induces greater leakage of cytoplasmic protein with carbonate. (B) LL-37 induces greater leakage of cytoplasmic protein with carbonate.
Figure 8:
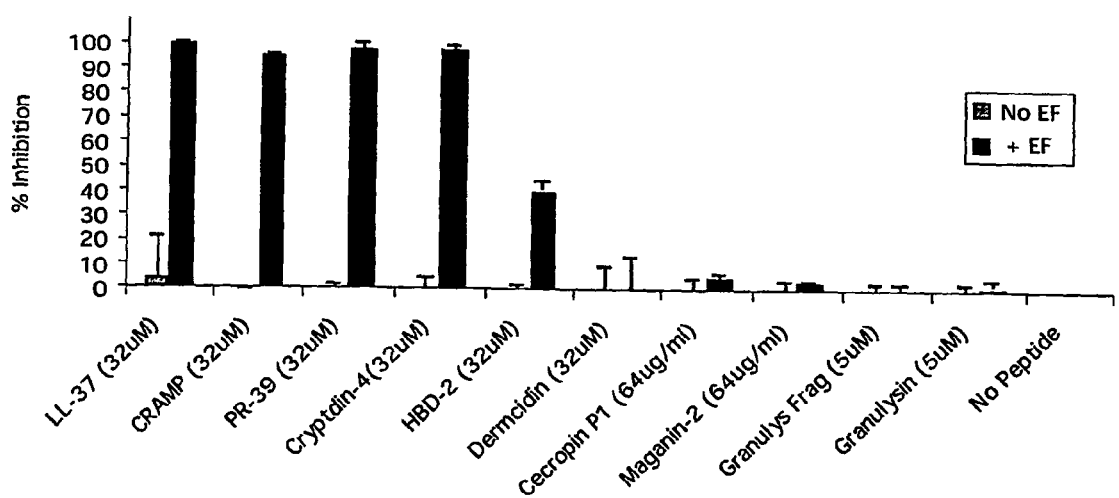
FIG. 8 shows that $NaHCO_3$ enhances the activity of various antimicrobial peptides (see also FIG. 4). The ability of 50 mM $NaHCO_3$ (EF) to enhance the activity of diverse antimicrobial peptides against *S. aureus* was tested in 20% TSB, 10% FBS, 1 mM $NaH_2PO_4$, 150 mM NaCl, pH 7.4. The activity of all 3 Cathelicidins, Cryptdin-4 and Human Beta Defensin-2 (HBD-2) were enhanced by the addition of bicarbonate. Several other antimicrobial peptides were not enhanced.
Figure 9:
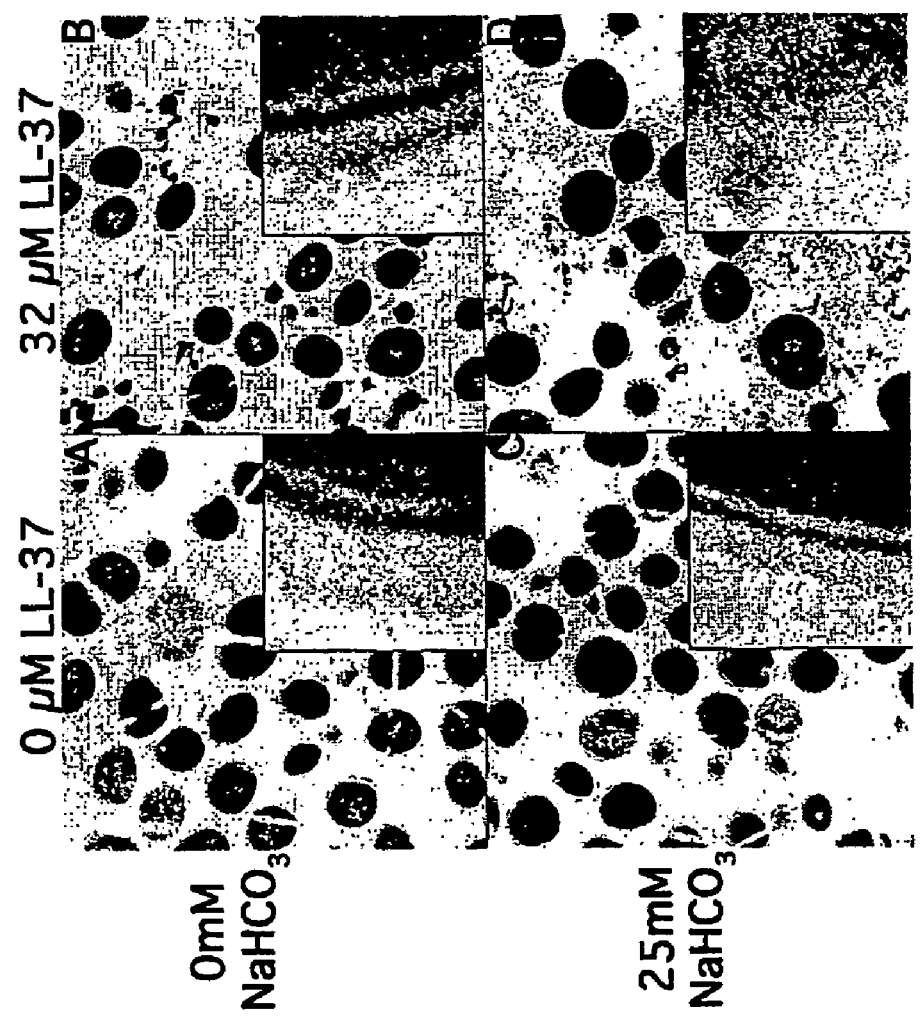
FIG. 9 is an electron microscopy micrograph showing bacterial cell wall lysis by LL-37 and bicarbonate. *S. aureus* was grown for four hours in 20% TSB, 1 mM $NaH_2PO_4$ with or without 25 mM $NaHCO_3$ or 32 uM LL-37. Bacteria were fixed in Karnovsky's Solution 24 hours and processed for EM on a Zeiss EM 10B Transmission Electron Microscope. The presence of 25 mm $NaHCO_3$ alone had no visible effect on the bacterial cell wall. 32 µM LL-37 caused a small amount of damage to bacterial cell walls in the absence of $NaHCO_3$, but totally ablated them in its presence, causing cell lysis. Mag 42,000×, insets are 110,000×.

FIG. 13A-D shows the identification of novel cathelicidin peptides generated from LL-37. Following purification shown in FIG. 3, major bioactive fractions were identified. a) peak (1) in FIG. 12a identified as KR-20 by mass spec. (MW 2468), and N-terminal sequence KRIVQRIKDVF (SEQ ID NO:2), b) peak (2) detected 2 peptides; RK-31 and KS-30 (MW 3647, 3803, and RKSKEKIG (SEQ ID NO:3), KSKEKIGK (SEQ ID NO:4), respectively), c) Western blot analysis with anti-LL-37 was done on all fractions from FIG. 3, shown are fractions eluting at acetonitrile concentrations 46-55. Peaks labeled (2) and (3) in FIG. 3 were immunoreactive. d) peak (3) identified as LL-37 (MW 4493). Data from single experiment representative of 3.

Figure 14:
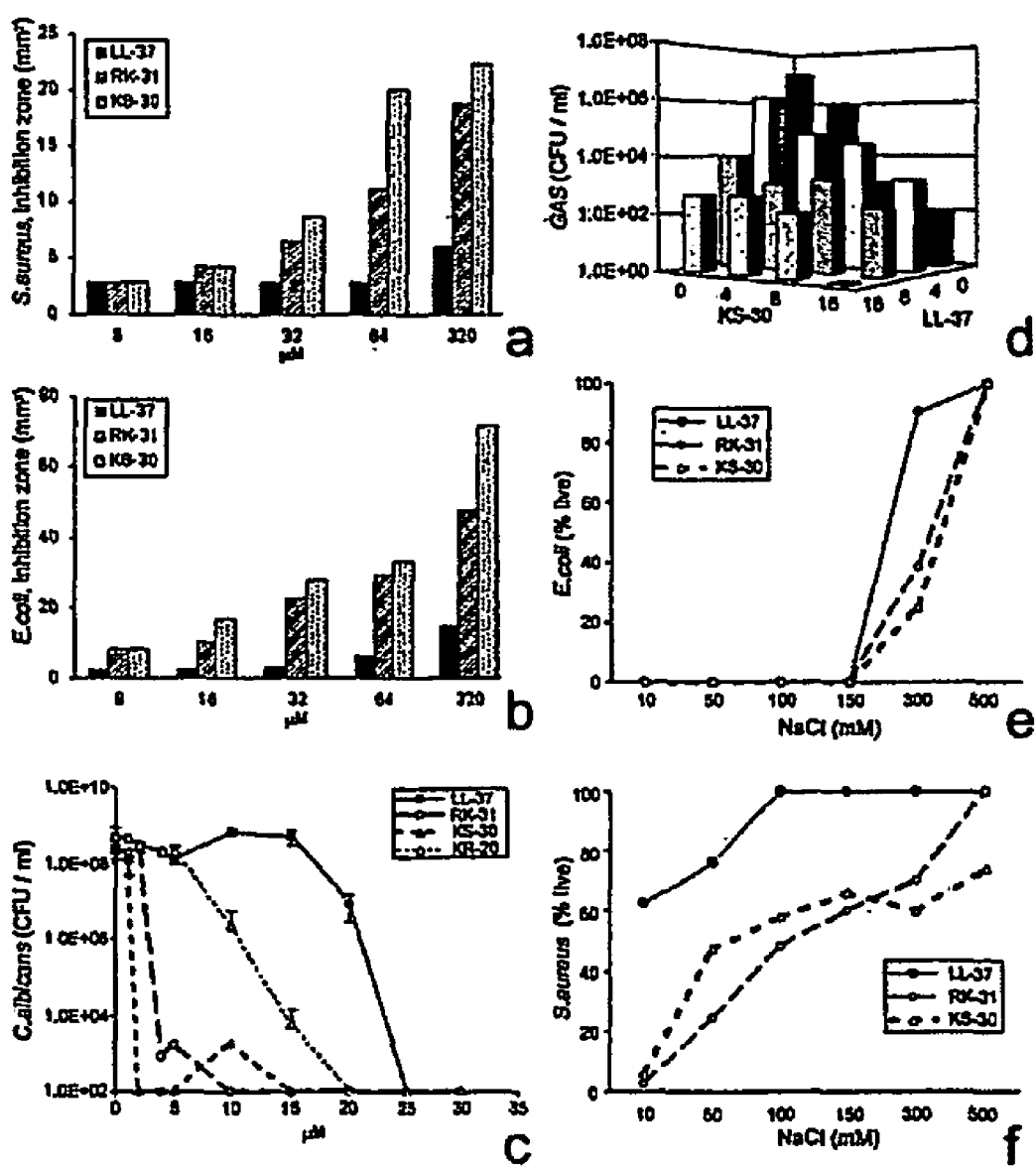

FIG. 14 shows the processing of LL-37 enhances antimicrobial activity. The antimicrobial activity of cathelicidin peptides was evaluated by radial diffusion assay against (a) *S. aureus*, (b) *E. coli*, (c) solution assay against *C. albicans* and (d) Group A Streptococci. The antimicrobial activity of each peptide was evaluated in 10% TSB/10 mM phosphate buffer with several NaCl concentraions against *E. coli* (e) and *S. aureus* (f). Data shown are representative of triplicate determinations.

Figure 15:
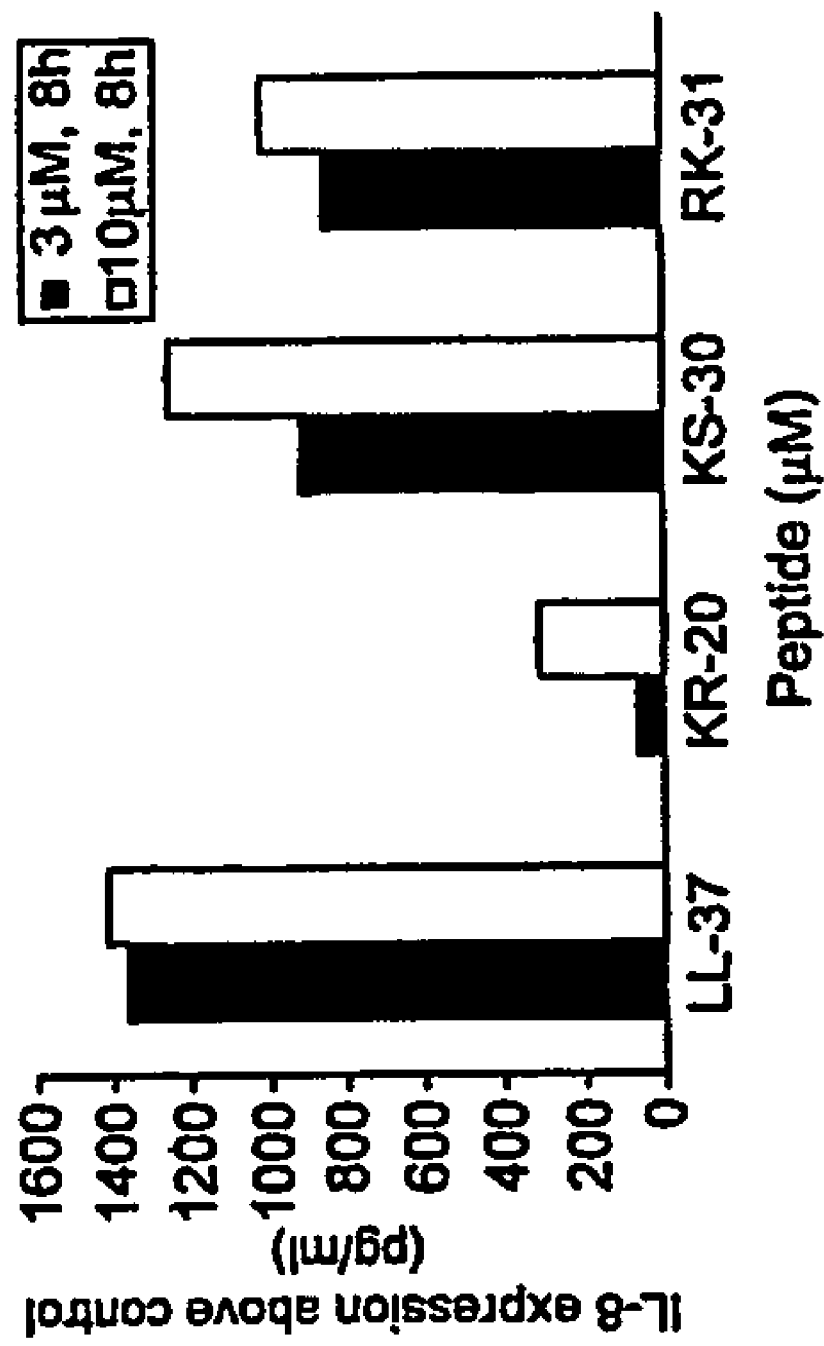

FIG. 15 shows that processing of LL-37 decreases ability to stimulate keratinocyte IL-8. Cathelicidin peptides were added to culture of normal human keratinocytes at a final concentration of 3 or 10 mM then IL-8 release determined after 8 hr. All samples were endotoxin free by *limulus* assay. Data are mean±SEM of triplicate determinations.

Figure 16:
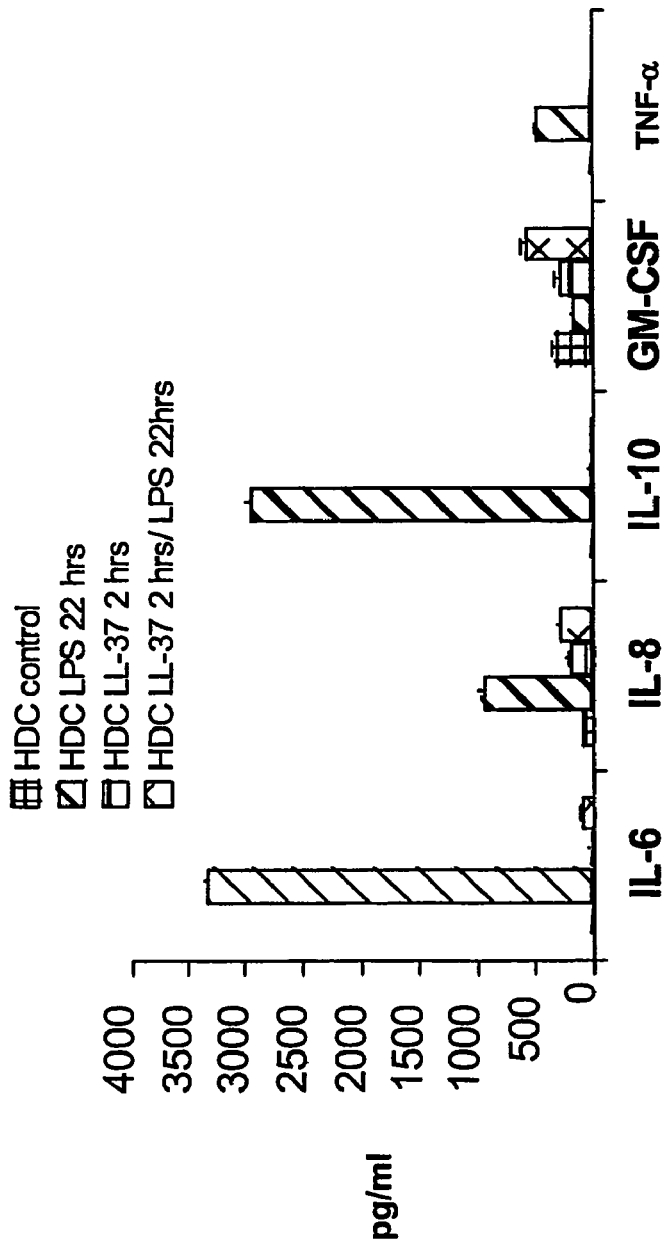

FIG. 16 is a graph showing that LL-37 induces neutrophil and mast cell chemotaxis.

Figure 17:
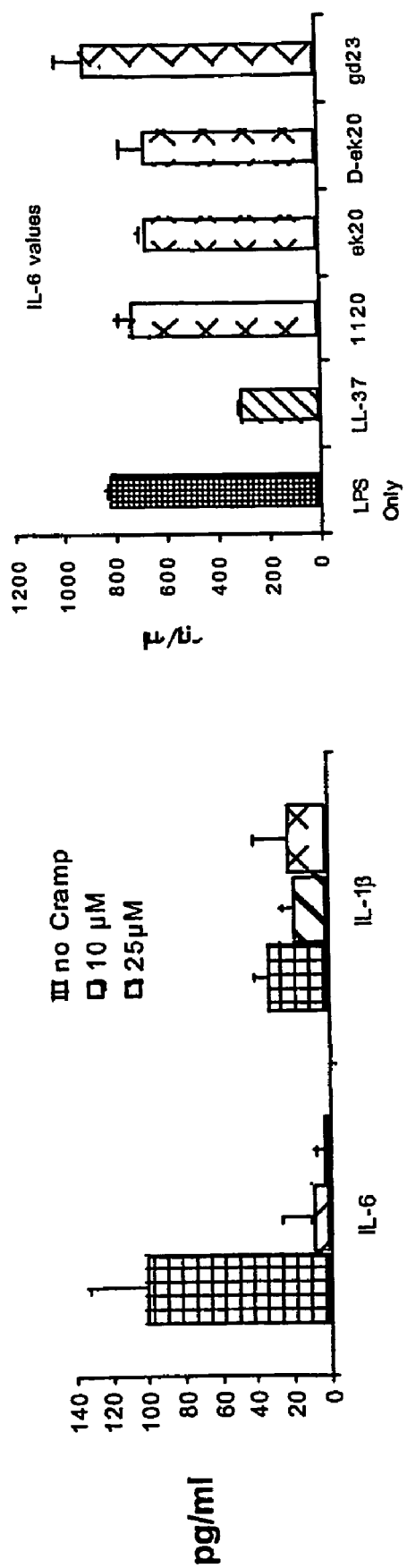

FIG. 17 is a graph showing that CRAMP has similar effect in mouse dendritic cells.

Figure 18A:
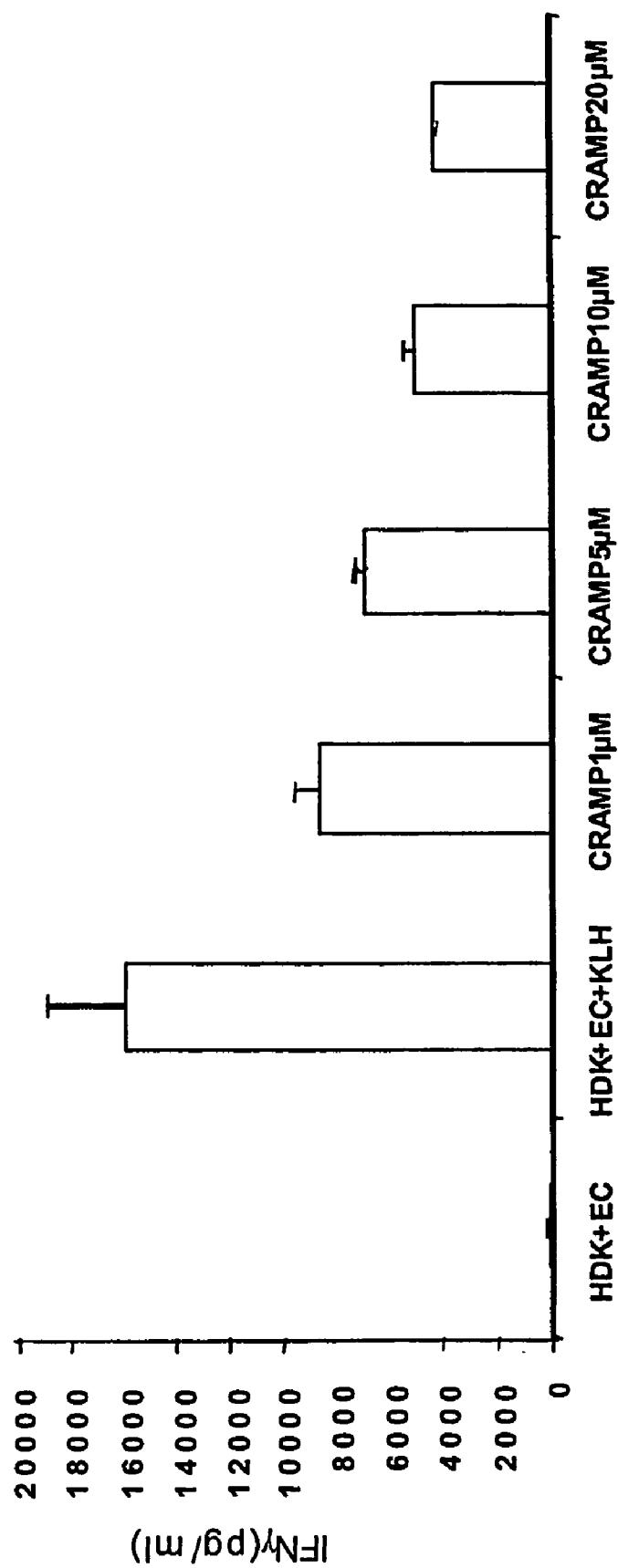
Figure 18B:
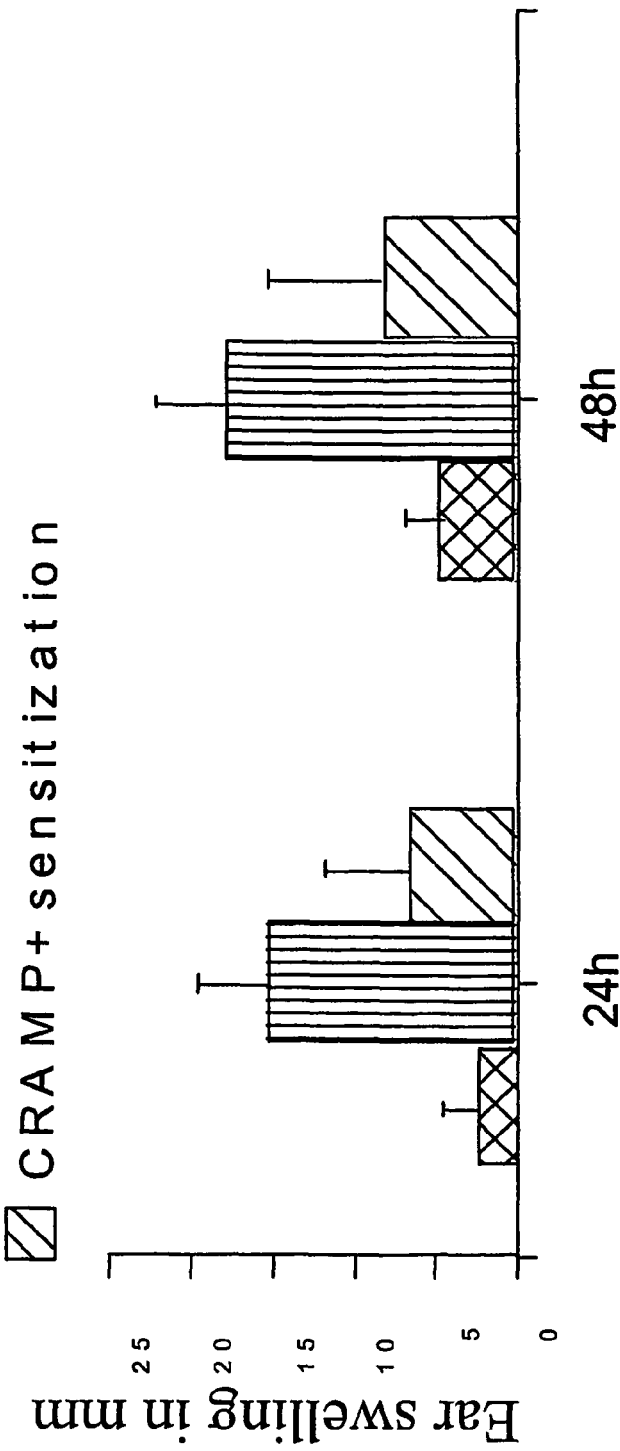
Figure 18C:
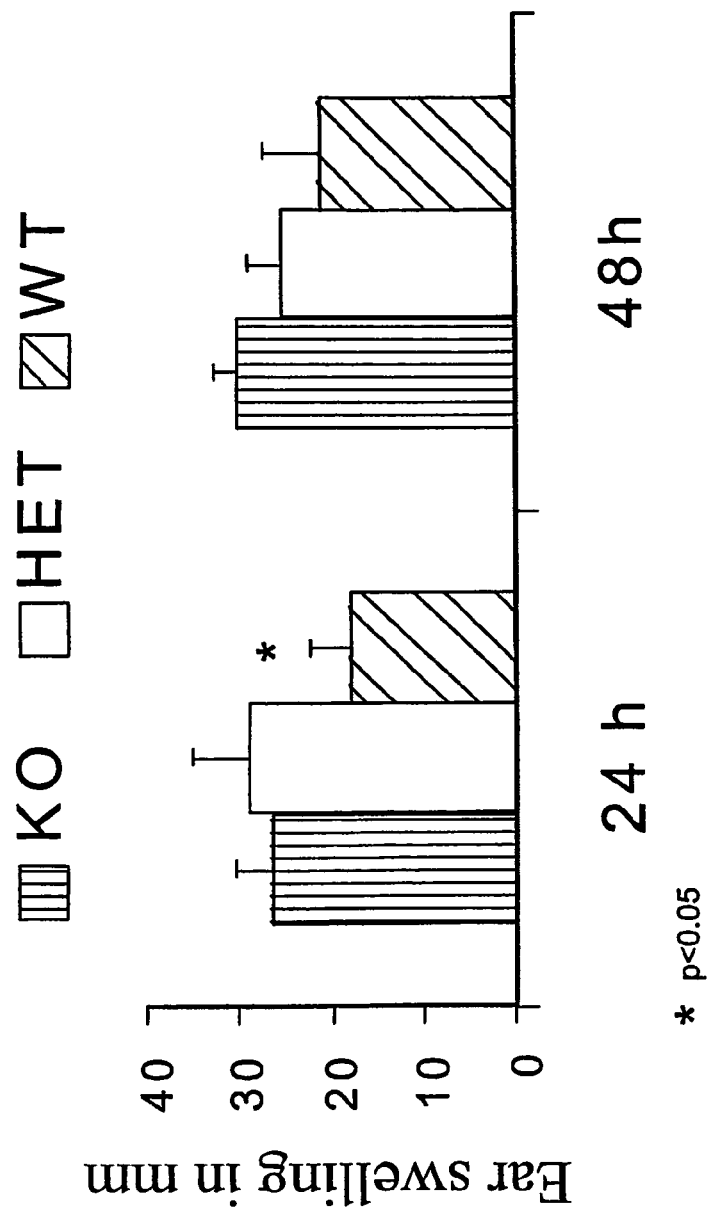

FIG. 18A-C show that CRAMP inhibits antigen presentation in vitro.

FIG. 19A-D shows the identification of cathelicidin function fragments on the normal skin surface by HPLC.

Figure 20:
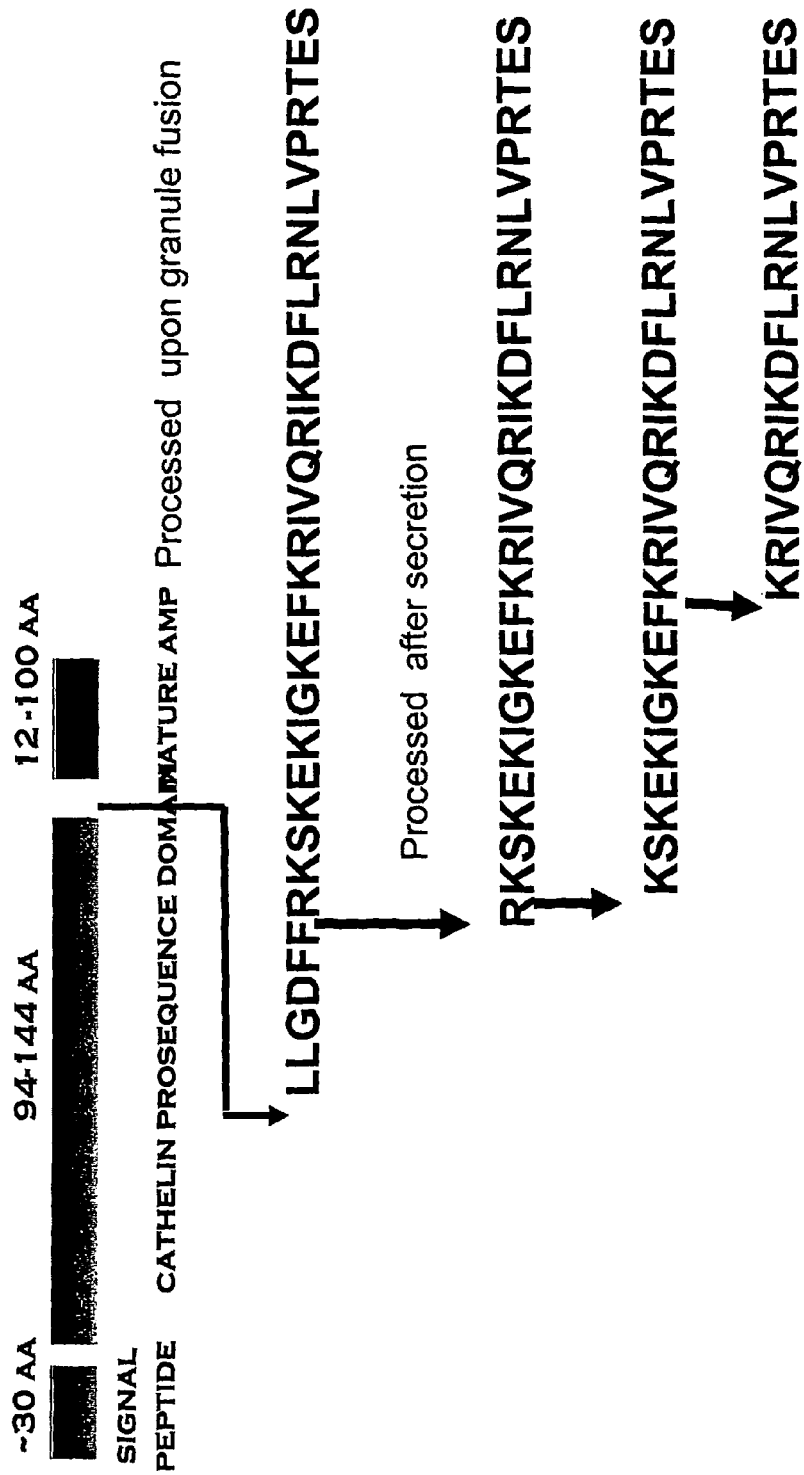

FIG. 20 shows a schematic of cathelicidin processing on the normal skin surface.

DETAILED DESCRIPTION

So long as there is an apparent need for protection against infection the evaluation of host responses that contribute to control of bacterial and viral infections in general is an important goal. The disclosure provides peptides useful in treating bacterial, viral and other microbial infections.

In humans, there are several classes of known antimicrobial peptides (AMPs) including α-defensins, β-defensins, and cathelicidins. Cathelicidins are found in several mammalian species. Production of cathelicidins is induced in response to epithelial wounding or infectious challenge, or suppressed by the virulence mechanisms of certain bacterial pathogens, e.g., *Shigella dysenteriae*. Cathelicidin expression is also differentially effected in certain chronic inflammatory disorders. In psoriasis, cathelicidin levels are elevated and secondary infection is rare, whereas in atopic dermatitis cathelicidin expression is deficient and bacterial or viral superinfection is common. Therapeutic benefits of cathelicidin have been demonstrated experimentally, including decreased bacterial colonization of skin wounds following topical administration and improved pulmonary bacterial clearance with cathelicidin overexpression through viral gene transfer.

Cathelicidin proteins are composed of two distinct domains: an N-terminal "cathelin-like" or "prosequence" domain and the C-terminal domain of the mature AMP. The C-terminal domains of cathelicidins were among the earliest mammalian AMPs to show potent, rapid, and broad-spectrum killing activity. The term "cathelin-like" derives from the similarity of the N-terminal sequence with that of cathelin, a 12 kDa protein isolated from porcine neutrophils that shares similarity with the cystatin superfamily of cysteine protease inhibitors.

Cathelicidins are expressed in neutrophils and myeloid bone marrow cells and most epithelial sources, and were the first AMPs discovered in mammalian skin due to their presence in wound fluid. In the neutrophil, cathelicidins are synthesized as full-length precursor and targeted to the secondary granules where they are stored. Upon stimulation, the full-length cathelicidin protein is proteolytically processed to unleash the microbicidal activity of the C-terminal peptide from the cathelin-like domain.

The C-terminal 37 amino acids of human cathelicidin (LL-37) has been characterized. LL-37 was originally referred to as FALL39, named for the first 4 N-terminal amino acids of this domain and the total number of residues (i.e., 39). LL-37 is a peptide predicted to contain an amphipathic alpha helix and lacks cysteine, making it different from all other previously isolated human peptide antibiotics of the defensin family, each of which contain 3 disulfide bridges. Full length human cathelicidin (sometimes referred to as full length LL-37) comprises the cathelin-like precursor protein and the C-terminal LL-37 peptide, thus comprising 170 amino acids (SEQ ID NO:6).

The polypeptide comprising SEQ ID NO:6 has a number of distinct domains. For example, a signal domain comprising a sequence as set forth from about 1 to about 29-31 of SEQ ID NO:6 is present. The signal domain is typically cleaved following amino acid number 30 of SEQ ID NO:6, however, one of skill in the art will recognize that depending upon the enzyme used, the expression system used and/or the conditions under which proteolytic cleavage of the polypeptide takes place, the cleavage site may vary from 1 to 3 amino acid in either direction of amino acid number 30 of SEQ ID NO:6. Another domain comprises the N-terminal domain, referred to as the cathelin-like doman. The cathelin-like domain comprises from about amino acid 29 (e.g., 29-31) to about amino acid 128 (e.g., 128-131) of SEQ ID NO:6. Yet another domain of SEQ ID NO:6 comprises the C-terminal domain referred to as LL-37. The LL-37 domain comprises from about amino acid 128 (e.g., 128-134) to amino acid 170 of SEQ ID NO:6.

LL-37 comprises the amino acid sequence set forth in SEQ ID NO:6. The human cDNA sequence for LL-37 is set forth in SEQ ID NO:5. The coding sequence of an active fragment of LL-37 can be identified with reference to the cDNA sequence provided in SEQ ID NO:5 without difficulty. Accordingly the corresponding coding sequences of the fragments identified herein are also provided by the disclosure.

The disclosure demonstrates human and murine C-terminal domains of cathelicidins, and functional fragments thereof, have antimicrobial and antiviral activity in vitro and in vivo.

The invention demonstrates that a minimal peptide domain of the C-terminal of cathelicidins comprising specific structural elements have antibacterial, antiviral and/or antimicrobial effects. The mechanisms by which cationic human antimicrobial peptides kill bacteria and fungi are generally through binding of the peptide to the microbial cell membrane, after which the membrane's proton gradient and integrity are lost.

The invention provides a peptide consensus sequence found in a number of peptides which inhibit bacterial growth and/or viral growth and mimic the activity of LL-37, CRAMP, and/or FALL-39. This consensus sequence is 18 amino acids in length and is found in LL-37, CRAMP and FALL-39. The consensus sequences corresponds to amino acids 151-166 of full-length LL-37 (SEQ ID NO:6), and amino acids 154-169 of CRAMP (SEQ ID NO:8). The peptides of the invention consist of 16-36 amino acids and contain $NH_2-X_1X_2X_3X_4X_5X_6IKX_7FX_8X_9X_{10}LX_{11}X_{12}-COOH$ (SEQ ID NO:1), wherein $X_1$, $X_2$, and $X_6$ are individually K or R; wherein $X_3$ is I or K; wherein $X_4$ is V or G; wherein $X_5$ is Q or R; wherein $X_7$ is any amino acid; wherein $X_8$ is L or F; wherein $X_a$ is R or Q; $X_{10}$ is N or K; $X_{11}$ is V or A; and wherein $X_{12}$ is P or L. A pile up of related cathelicidin proteins is provided in FIG. 1.

In one aspect, the invention provides active fragments of LL-37 and CRAMP that inhibit bacterial growth and viral infection. For example, active fragments of LL-37 include SEQ ID NO:6 from about amino acid $XX_1$ to $XX_2$, wherein $XX_1$ is an amino acid between and including 135 and 151 (i.e., 135, 136, 137, 138, 139, 140, 141, 142, 143, 144, 145, 146, 147, 148, 149, 150, and 151) and wherein $XX_2$ is an amino acid between and including 166 and 170 (i.e., 166, 167, 168, 169, and 170). Table 1 sets forth exemplary sequence of cathelicidin functional fragments.

TABLE 1

| Sequence | SEQ ID NO:6 from aa to aa |
|---|---|
| RKSKEKIGKEFKRIVQRIKDFLRNLVPRTES | 141 to 170 (SEQ ID NO:27) |
| KSKEKIGKEFKRIVQRIKDFLRNLVPRTES | 142 to 170 (SEQ ID NO:22) |
| KRIVQRIKDFLRNLVPRTES | 151 to 170 (SEQ ID NO:17) |

Figure 1:
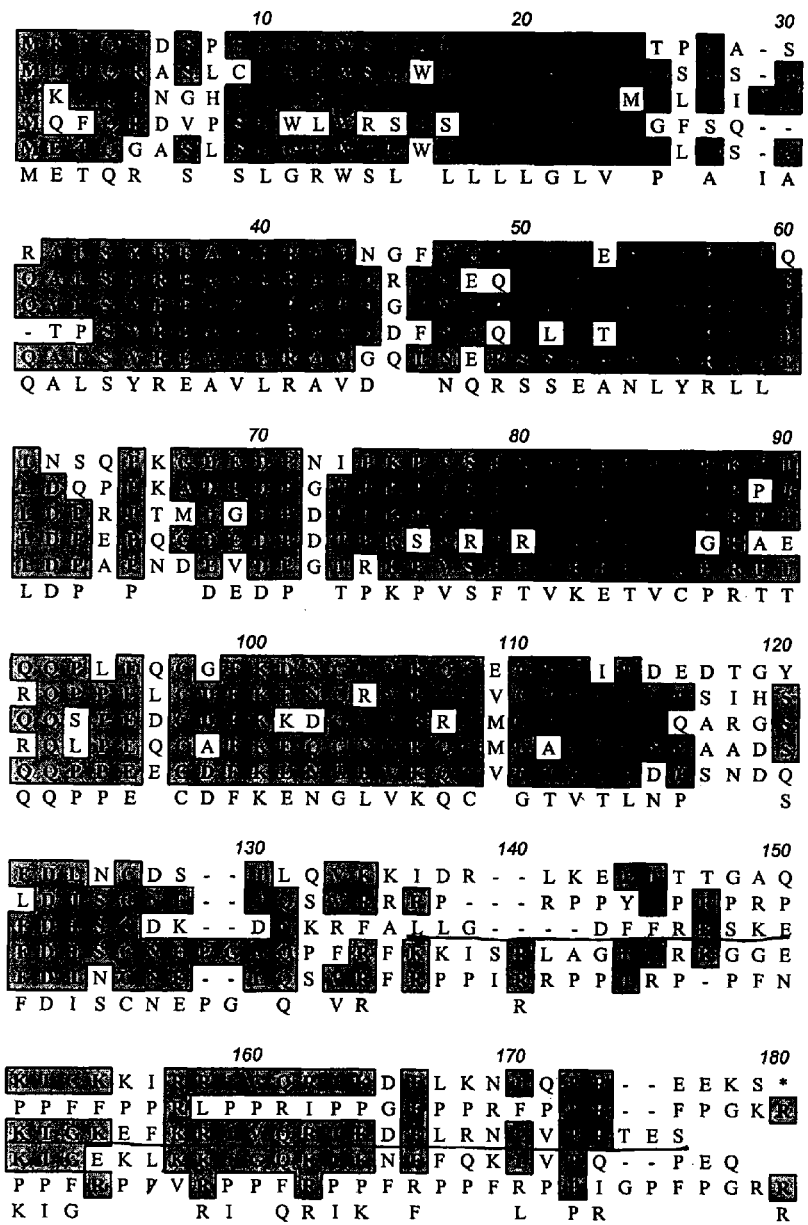
FIG. 1 shows a pile up of protein sequence from canine cathelicidin (SEQ ID NO:9), PR-39 (SEQ ID NO:10); LL-37 (SEQ ID NO:6), murine CRAMP (SEQ ID NO:8) and goat cathelecidin (SEQ ID NO:11).
Figure 2:
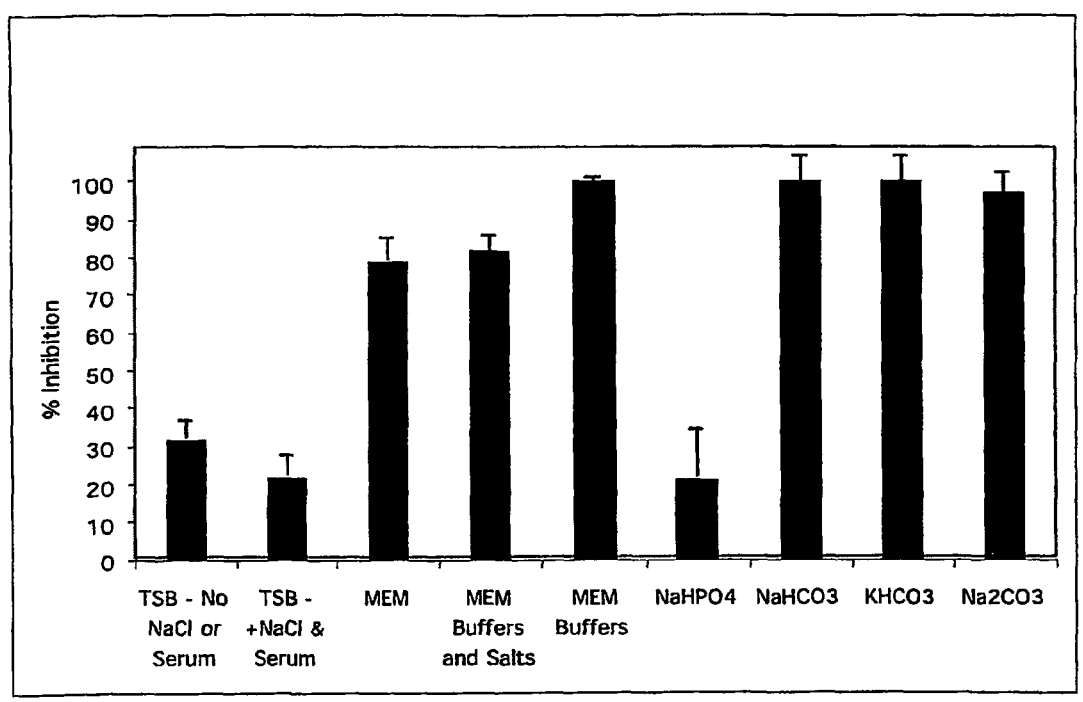
FIG. 2 shows that carbonate containing compounds increase the antimicrobial activity of LL-37. Carbonate was identified as the antimicrobial enhancing factor in mammalian tissue culture media via serial deletion of Minimal Essential Media (MEM) components. Staphylococcus aureus was cultured in 20% Tryptic Soy Broth (TSB), 10% Fetal Bovine Serum (FBS) and 70% of various media or media components with, or without, 32 μM LL-37 to assess which components could increase antimicrobial activity. MEM buffers are 2200 mg/L $NaHCO_3$, 140 mg/L $NaH_2PO_4$ and 6800 mg/L NaCl. MEM salts are 200 mg/L $CaCl_2$, 400 mg/L KCl, 98 mg/L $MgSO_4$. All solutions were adjusted to pH 7.4. Bacterial growth was measured as the change in turbidity at $OD_{600}$ and percent inhibition was determined by comparing bacterial growth in the presence of peptide to that in the absence of peptide. 32 μM LL-37 inhibited Staphalococcus aureus growth poorly in TSB media alone, or with NaCl and FBS. In the presence of MEM buffers, inhibition was greatly increase and $NaHCO_3$, was determined to be the buffering component responsible for this increase. This was confirmed with other carbonate containing compounds, 50 mM $KHCO_3$ and $Na_2CO_3$, which also increased antimicrobial activity.

The pile up alignments of FIG. 1 are useful in identifying amino acids that may be substituted (i.e., that are not highly conserved) in peptide fragments of the invention. For example, with reference to FIG. 1 it will be apparent that bolded amino acids are conserved compared to the amino acids presented in regular text. Accordingly, substitutions of amino acid at places in the peptide in regular text will likely be tolerated in contrast to non-conservative substitutions of bolded amino acids.

The term "antimicrobial" as used herein means that the peptide destroys, or inhibits or prevents the growth or proliferation of, a microbe (e.g., a bacterium, fungus, and/or virus). Likewise, the term "antiviral" as used herein means that a peptide destroys, or inhibits or prevents the growth or proliferation of a virus or a virus-infected cell. The term "antitumor" as used herein means that a peptide prevents, inhibits the growth of, or destroys, a tumor cell(s). Similarly, the term "antifungal" means that a peptide prevents, destroys, or inhibits the growth of a fungus.

As used herein, the term "cathelicidin functional fragment" refers to a chain of amino acids that is about 16 to 36 amino acids in length and (i) contains a sequence as set forth in SEQ ID NO:1, (ii) is a fragment of the C-terminus of SEQ ID NO:6 containing SEQ ID NO:1, (iii) is an active fragment of LL-37 from about amino acid $XX_1$ to $XX_2$ of SEQ ID NO:6, wherein $XX_1$ is an amino acid between and including 135 and 151 (i.e., 135, 136, 137, 138, 139, 140, 141, 142, 143, 144, 145, 146, 147, 148, 149, 150, and 151) and wherein $XX_2$ is an amino acid between and including 166 and 170 (i.e., 166, 167, 168, 169, and 170), or (iv) a fragment set forth in Table 1. A peptide is "cationic" if it has a pKa greater than 9.0. Typically, at least four of the amino acid residues of the cationic peptide are positively charged residues, e.g., lysine and arginine. "Positively charged" refers to the side chain of an amino acid residue that has a net positive charge at pH 7.0.

The term "purified" and "substantially purified" as used herein refers to a polypeptide or peptide that is substantially free of other proteins, lipids, and polynucleotides (e.g., cellular components with which an in vivo-produced polypeptide or peptide would naturally be associated). Typically, the peptide is at least 70%, 80%, or most commonly 90% pure by weight.

The disclosure also includes analogs, derivatives, conservative variations, and cathelicidin functional fragment variants of the enumerated cathelicidin functional fragments, provided that the analog, derivative, conservative variation, or variant has a detectable antimicrobial antibacterial and/or antiviral activity. It is not necessary that the analog, derivative, variation, or variant have activity identical to the activity of the peptide from which the analog, derivative, conservative variation, or variant is derived. For example, using the alignment provided in FIG. 1, one of skill in the art can readily identify conserved amino acids and non-conserved amino acid. Using the alignment, one of skill in the art can readily identify which amino acid may be modified or substituted.

A cathelicidin functional fragment "variant" is an antimicrobial, antibacterial and/or antiviral peptide that is an altered form of a referenced cathelicidin functional fragment. For example, the term "variant" includes a cathelicidin functional fragment produced by the method disclosed herein in which at least one amino acid (e.g., from about 1 to 10 amino acids) of a reference peptide is substituted with another amino acid. The term "reference" peptide means any of the cathelicidin functional fragments of the disclosure (e.g., as defined in the above formula (SEQ ID NO:1) as well as the specific fragments described in Table 1 from which a variant, derivative, analog, or conservative variation is derived. Included within the term "derivative" is a hybrid peptide that includes at least a portion of each of two cathelicidin functional fragments (e.g., 30-80% of each of two cathelicidin functional fragments). Derivatives can be produced by adding one or a few (e.g., 1-5) amino acids to a peptide of the disclosure without completely inhibiting the activity of the peptide. In addition, C-terminal derivatives, e.g., C-terminal methyl esters, can be produced and are encompassed by the disclosure.

The disclosure also includes peptides that are conservative variations of those peptides as exemplified herein. The term "conservative variation" as used herein denotes a peptide or polypeptide in which at least one amino acid is replaced by another, biologically similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acid, or glutamine for asparagine, and the like. Neutral hydrophilic amino acids that can be substituted for one another include asparagine, glutamine, serine and threonine. The term "conservative variation" also encompasses a peptide having a substituted amino acid in place of an unsubstituted parent amino acid; typically, antibodies raised to the substituted peptide or polypeptide also specifically bind the unsubstituted peptide or polypeptide.

Cathelicidin functional fragment variants of the disclosure can be identified by screening a large collection, or library, of random peptides or polypeptides using, for example, one of a number of animal models such as CRAMP knockout mice that display increased susceptability to skin infections. Cathelicidin functional fragment variants can be, for example, a population of peptides related in amino acid sequence to SEQ ID NO:1 by having various substitutions based upon, for example, the sequences as set forth in the pile up of FIG. 1, and the sequence set forth in Table 1.

Peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid, which encodes it. Methods for the production of phage display libraries, including vectors and methods of diversifying the population of peptides, which are expressed, are known in the art (see, for example, Smith and Scott, Methods Enzymol. 217:228-257 (1993); Scott and Smith, Science 249:386-390 (1990); and Huse, WO 91/07141 and WO 91/07149). These or other known methods can be used to produce a phage display library, from which the displayed peptides can be cleaved and assayed for antibacterial activity. If desired, a population of peptides can be assayed for activity, and an active population can be subdivided and the assay repeated in order to isolate an active peptide from the population. Other methods for producing peptides useful in the disclosure include, for example, rational design and mutagenesis based on the amino acid sequences of a cathelicidin functional fragment as set forth in SEQ ID NO:1 and 6 and Table 1, for example.

A cathelicidin functional fragment variant can be a peptide mimetic, which is a non-amino acid chemical structure that mimics the structure of, for example, a cathelicidin functional fragment of SEQ ID NO:1 and the related peptides of Table 1, yet retains antimicrobial/antibacterial/antiviral. Such a mimetic generally is characterized as exhibiting similar physical characteristics such as size, charge or hydrophobicity in the same spatial arrangement found in the cathelicidin functional fragment counterpart. A specific example of a peptide mimetic is a compound in which the amide bond between one or more of the amino acids is replaced, for example, by a carbon-carbon bond or other bond well known in the art (see, for example, Sawyer, Peptide Based Drug Design, ACS, Washington (1995)).

The amino acids of a cathelicidin functional fragment, cathelicidin functional fragment variant or peptidomimetic of the disclosure are selected from the twenty naturally occurring amino acids, including, unless stated otherwise, L-amino acids and D-amino acids. The use of D-amino acids are particularly useful for increasing the life of a peptide or polypeptide. Polypeptides or peptides incorporating D-amino acids are resistant to proteolytic digestion. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains its biological activity. For example, glutamine can be an amino acid analog of asparagine, provided that it can be substituted within an active fragment of a cathelicidin functional fragment, variant and the like such that it retains its antimicrobial/antibacterial/antiviral activity. Other examples of amino acids and amino acids analogs are listed in Gross and Meienhofer, The Peptides: Analysis, Synthesis, Biology, Academic Press, Inc., New York (1983). An amino acid also can be an amino acid mimetic, which is a structure that exhibits substantially the same spatial arrangement of functional groups as an amino acid but does not necessarily have both the "-amino" and "-carboxyl" groups characteristic of an amino acid.

Peptides of the disclosure can be synthesized by commonly used methods such as those that include t-BOC or FMOC protection of alpha-amino groups. Both methods involve stepwise synthesis in which a single amino acid is added at each step starting from the C terminus of the peptide (See, Coligan, et al., Current Protocols in Immunology, Wiley Interscience, 1991, Unit 9). Peptides of the disclosure can also be synthesized by the well known solid phase peptide synthesis methods such as those described by Merrifield, J. Am. Chem. Soc., 85:2149, 1962; and Stewart and Young, Solid Phase Peptides Synthesis, Freeman, San Francisco, 1969, pp. 27-62, using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with a 1% acetic acid solution, which is then lyophilized to yield the crude material. The peptides can be purified by such techniques as gel filtration on Sephadex G-15 using 5% acetic acid as a solvent. Lyophilization of appropriate fractions of the column eluate yield homogeneous peptide, which can then be characterized by standard techniques such as amino acid analysis, thin layer chromatography, high performance liquid chromatography, ultraviolet absorption spectroscopy, molar rotation, or measuring solubility. If desired, the peptides can be quantitated by the solid phase Edman degradation.

The activity of the peptides of the disclosure can be determined using conventional methods known to those of skill in the art, such as in a "minimal inhibitory concentration (MIC)", whereby the lowest concentration at which no change in OD is observed for a given period of time is recorded as the MIC. Alternatively, a "fractional inhibitory concentration (FIC)" assay can be used to measure synergy between the peptides of the disclosure, or the peptides in combination with known antibiotics. FICs can be performed by checkerboard titrations of peptides in one dimension of a microtiter plate, and of antibiotics in the other dimension, for example. The FIC is a function of the impact of one antibiotic on the MIC of the other and vice versa. A FIC of 1 indicates that the influence of the compounds is additive and a FIC of less than 1 indicates that the compounds act synergistically.

Peptides of the disclosure can be synthesized by commonly used methods such as those that include t-BOC or FMOC protection of alpha-amino groups. Both methods involve stepwise synthesis in which a single amino acid is added at each step starting from the C-terminus of the peptide (See, Coligan, et al., Current Protocols in Immunology, Wiley Interscience, 1991, Unit 9). Peptides of the disclosure can also be synthesized by the well known solid phase peptide synthesis methods such as those described by Merrifield, J. Am. Chem. Soc., 85:2149, 1962; and Stewart and Young, Solid Phase Peptides Synthesis, Freeman, San Francisco, 1969, pp. 27-62) using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with a 1% acetic acid solution, which is then lyophilized to yield the crude material. The peptides can be purified by such techniques as gel filtration on Sephadex G-15 using 5% acetic acid as a solvent. Lyophilization of appropriate fractions of the column eluate yield homogeneous peptide, which can then be characterized by standard techniques such as amino acid analysis, thin layer chromatography, high performance liquid chromatography, ultraviolet absorption spectroscopy, molar rotation, or measuring solubility. If desired, the peptides can be quantitated by the solid phase Edman degradation.

The disclosure also includes isolated polynucleotides (e.g., DNA, cDNA, or RNA) encoding the peptides of the disclosure. Included are polynucleotides that encode analogs, mutants, conservative variations, and variants of the peptides described herein. The term "isolated" as used herein refers to a polynucleotide that is substantially free of proteins, lipids, and other polynucleotides with which an in vivo-produced polynucleotide naturally associates. Typically, the polynucleotide is at least 70%, 80%, or 90% isolated from other matter, and conventional methods for synthesizing polynucleotides in vitro can be used in lieu of in vivo methods. As used herein, "polynucleotide" refers to a polymer of deoxyribonucleotides or ribonucleotides, in the form of a separate fragment or as a component of a larger genetic construct (e.g., by operably linking a promoter to a polynucleotide encoding a peptide of the disclosure). Numerous genetic constructs (e.g., plasmids and other expression vectors) are known in the art and can be used to produce the peptides of the disclosure in cell-free systems or prokaryotic or eukaryotic (e.g., yeast, insect, or mammalian) cells. By taking into account the degeneracy of the genetic code, one of ordinary skill in the art can readily synthesize polynucleotides encoding the peptides of the disclosure. The polynucleotides of the disclosure can readily be used in conventional molecular biology methods to produce the peptides of the disclosure.

In one embodiment, a cathelicidin functional fragment polynucleotide/nucleic acid of the disclosure comprises a sequence of SEQ ID NO:5. In one aspect, a polynucleotide encoding a cathelicidin function fragment comprises SEQ ID NO:5 from about nucleotide 451 to 498, from about nucleotide 451 to 501, from about nucleotide 451 to 504, from about nucleotide 451 to 507, from about nucleotide 451 to 510, from about nucleotide 421 to 498, from about nucleotide 421 to 501, from about nucleotide 421 to 504, from about nucleotide 421 to 507, from about nucleotide 421 to 510, from about nucleotide 418 to 498, from about nucleotide 418 to 501, from about nucleotide 418 to 504, from about nucleotide 418 to 507, from about nucleotide 418 to 510, from about nucleotide 403 to 498, from about nucleotide 403 to 501, from about nucleotide 403 to 504, from about nucleotide 403 to 507, and from about nucleotide 403 to 510.

```
  1taaagcaaac cccagcccac accctggcag    (SEQ ID NO:5)
   gcagccaggg atgggtggat caggaaggct 61cctggttggg cttttgcatc aggctcaggc
   tgggcataaa ggaggctcct gtgggctaga 121gggaggcaga catgggracc atgaagaccc
   aaagggatgg ccactccctg gggcggtggt 181cactggtgct cctgctgctg ggcctggtga
   tgcctctggc catcattgcc caggtcctca 241gctacaagga agctgtgctt cgtgctatag
   atggcatcaa ccagcggtcc tcggatgcta 301acctctaccg cctcctggac ctggacccca
   ggcccacgat ggatggggac ccagacacgc 361caaagcctgt gagcttcaca gtgaaggaga
   cagtgtgccc caggacgaca cagcagtcac 421cagaggattg tgacttcaag aaggacgggc
   tggtgaagcg gtgtatgggg acagtgaccc 481tcaaccaggc caggggctcc tttgacatca
   gttgtgataa ggataacaag agatttgccc 541tgctgggtga tttcttccgg aaatctaaag
   agaagattgg caaagagttt aaaagaattg 601tccagagaat caaggatttt ttgcggaatc
   ttgtacccag gacagagtcc tagtgtgtgc 661cctaccctgg ctcaggcttc tgggctctga
   gaaataaact atgagagcaa tttcaaaaaa 721aaaaaaaaaa aaaaaaaaa
```

In another example, a polynucleotide encoding a cathelicidin functional fragment of the disclosure comprises a sequence of SEQ ID NO:7. In one aspect, a polynucleotide encoding a cathelicidin functional fragment comprises SEQ ID NO:7 from about nucleotide 460 to nucleotide 507.

```
  1atgcagttcc agagggacgt cccctccctg    (SEQ ID NO:7)
   tggctgtggc ggtcactatc actgctgctg 61ctactgggcc tggggttctc ccagaccccc
   agctacaggg atgctgtgct ccgagctgtg 121gatgacttca accagcagtc cctagacacc
   aatctctacc gtctcctgga cctggatcct 181gagccccaag gggacgagga tccagatact
   cccaagtctg tgaggttccg agtgaaggag 241actgtatgtg gcaaggcaga gcggcagcta
   cctgagcaat gtgccttcaa ggaacagggg 301gtggtgaagc agtgtatggg ggcagtcacc
   ctgaacccgg ccgctgattc ttttgacatc
```

```
                    -continued
361agctgtaacg agcctggtgc acagcccttt
   cggttcaaga aaatttcccg gctggctgga 421cttctccgca aaggtgggga gaagattggt
   gaaaagctta agaaaattgg ccagaaaatt 481aagaattttt ttcagaaact tgtccctcag
   ccagagtag
```

Such polynucleotides include naturally occurring, synthetic, and intentionally manipulated polynucleotides. For example, a cathelicidin functional fragment peptide or polynucleotide may be subjected to site-directed mutagenesis. A cathelicidin functional fragment polynucleotide includes sequences that are degenerate as a result of the genetic code. There are 20 natural amino acids, most of which are specified by more than one codon. Therefore, all degenerate nucleotide sequences are included so long as the amino acid sequence of a cathelicidin functional fragment peptide or variant encoded by the polynucleotide is functionally unchanged. Accordingly, a polynucleotide of the invention includes (i) a polynucleotide encoding a cathelicidin functional fragment; (ii) a polynucleotide encoding SEQ ID NO:1 or a variant thereof, or SEQ ID NO:2-4 or a variant thereof; (iii) a polynucleotide comprising SEQ ID NO:5 from about nucleotide 451 to 498, from about nucleotide 451 to 501, from about nucleotide 451 to 504, from about nucleotide 451 to 507, from about nucleotide 451 to 510, from about nucleotide 421 to 498, from about nucleotide 421 to 501, from about nucleotide 421 to 504, from about nucleotide 421 to 507, from about nucleotide 421 to 510, from about nucleotide 418 to 498, from about nucleotide 418 to 501, from about nucleotide 418 to 504, from about nucleotide 418 to 507, from about nucleotide 418 to 510, from about nucleotide 403 to 498, from about nucleotide 403 to 501, from about nucleotide 403 to 504, from about nucleotide 403 to 507, and/or from about nucleotide 403 to 510; (iv) a polynucleotide of (iii), wherein T is U; and (v) a polynucleotide comprising a sequence that is complementary to (iii) and (iv) above. It will be recognized that a cathelicidin functional fragment polynucleotide, may be operably linked to a second heterologous polynucleotide such as a promoter or a heterologous sequence encoding a desired peptide or polypeptide sequence.

The term "isolated" as used herein refers to a nucleic acid that is substantially free of proteins, lipids, and other nucleic acids with which an in vivo-produced nucleic acids naturally associated. Typically, the nucleic acid is at least 70%, 80%, 90% or more pure by weight, and conventional methods for synthesizing nucleic acids in vitro can be used in lieu of in vivo methods. As used herein, "nucleic acid" or "polynucleotide" refers to a polymer of deoxyribonucleotides or ribonucleotides, in the form of a separate fragment or as a component of a larger genetic construct (e.g., by operably linking a promoter to a nucleic acid encoding a peptide of the disclosure). Numerous genetic constructs (e.g., plasmids and other expression vectors) are known in the art and can be used to produce the peptides of the disclosure in cell-free systems or prokaryotic or eukaryotic (e.g., yeast, insect, or mammalian) cells. By taking into account the degeneracy of the genetic code, one of ordinary skill in the art can readily synthesize nucleic acids encoding the polypeptides of the disclosure. The nucleic acids of the disclosure can readily be used in conventional molecular biology methods to produce the peptides of the disclosure.

Polynucleotides encoding the cathelicidin functional fragments of the disclosure can be inserted into an "expression vector." The term "expression vector" refers to a genetic construct such as a plasmid, virus or other vehicle known in the art that can be engineered to contain a polynucleotide encoding a peptide or polypeptide of the disclosure. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the disclosure. Typically, the expression vector contains a replicon site and control sequences that are derived from a species compatible with the host cell.

Transformation or transfection of a host cell with a polynucleotide of the disclosure can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Suitable methods for transforming eukaryotic cells, such as electroporation and lipofection, also are known.

"Host cells" encompassed by of the disclosure are any cells in which the polynucleotides of the disclosure can be used to express the cathelicidin functional fragments of the disclosure. The term also includes any progeny of a host cell. Host cells, which are useful, include bacterial cells, fungal cells (e.g., yeast cells), plant cells and animal cells. For example, host cells can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology (1986)). As representative examples of appropriate hosts, there may be mentioned: fungal cells, such as yeast; insect cells such as *Drosophila* S2 and *Spodoptera* Sf9; animal cells such as CHO, COS or Bowes melanoma; plant cells, and the like. The selection of an appropriate host is deemed to be within the scope of those skilled in the art from the teachings herein.

Host cells can be eukaryotic host cells (e.g., mammalian cells). In one aspect, the host cells are mammalian production cells adapted to grow in cell culture. Examples of such cells commonly used in the industry are CHO, VERO, BHK, HeLa, CV1 (including Cos; Cos-7), MDCK, 293, 3T3, C127, myeloma cell lines (especially murine), PC12 and W138 cells. Chinese hamster ovary (CHO) cells are widely used for the production of several complex recombinant proteins, e.g. cytokines, clotting factors, and antibodies (Brasel et al., Blood 88:2004-2012, 1996; Kaufman et al., J. Biol Chem 263: 6352-6362, 1988; McKinnon et al., J Mol Endocrinol 6:231-239, 1991; Wood et al., J. Immunol 145:3011-3016, 1990). The dihydrofolate reductase (DHFR)-deficient mutant cell lines (Urlaub et al., Proc Natl Acad Sci USA 77:4216-4220, 1980) are the CHO host cell lines commonly used because the efficient DHFR selectable and amplifiable gene expression system allows high level recombinant protein expression in these cells (Kaufman, Meth Enzymol 185:527-566, 1990). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

Polynucleotides encoding the peptides of the disclosure can be isolated from a cell (e.g., a cultured cell), or they can be produced in vitro. A DNA sequence encoding a cathelicidin functional fragment of interest can be obtained by: 1) isolation of a double-stranded DNA sequence from genomic DNA; 2) chemical manufacture of a polynucleotide such that it encodes the cathelicidin functional fragment of interest; or 3) in vitro synthesis of a double-stranded DNA sequence by reverse transcription of mRNA isolated from a donor cell (i.e., to produce cDNA).

Included in the disclosure are polynucleotides that encode analogs, mutants, conservative variations, and variants of the peptides described herein. For example, an isolated polynucleotide encoding a cathelicidin functional fragment of the disclosure can comprise the sequence of SEQ ID NO:5 from about nucleotide 451 to 498, from about nucleotide 451 to 501, from about nucleotide 451 to 504, from about nucleotide 451 to 507, from about nucleotide 451 to 510, from about nucleotide 421 to 498, from about nucleotide 421 to 501, from about nucleotide 421 to 504, from about nucleotide 421 to 507, from about nucleotide 421 to 510, from about nucleotide 418 to 498, from about nucleotide 418 to 501, from about nucleotide 418 to 504, from about nucleotide 418 to 507, from about nucleotide 418 to 510, from about nucleotide 403 to 498, from about nucleotide 403 to 501, from about nucleotide 403 to 504, from about nucleotide 403 to 507, and from about nucleotide 403 to 510.

Such polynucleotides include naturally occurring, synthetic, and intentionally manipulated polynucleotides. For example, a cathelicidin functional fragment or variant polynucleotide may be subjected to site-directed mutagenesis. A cathelicidin functional fragment or variant polynucleotide includes sequences that are degenerate as a result of the genetic code. There are 20 natural amino acids, most of which are specified by more than one codon. Therefore, all degenerate nucleotide sequences are included so long as the amino acid sequence of a cathelicidin functional fragment or variant encoded by the nucleotide sequence is functionally unchanged. Accordingly, a polynucleotide of the disclosure includes (i) a polynucleotide encoding a cathelicidin functional fragment or variant; (ii) a polynucleotide encoding SEQ ID NO:1 or a variant thereof, or SEQ ID NO:2-4 or a variant thereof; (iii) a polynucleotide comprising SEQ ID NO:5 from about nucleotide 451 to 498, from about nucleotide 451 to 501, from about nucleotide 451 to 504, from about nucleotide 451 to 507, from about nucleotide 451 to 510, from about nucleotide 421 to 498, from about nucleotide 421 to 501, from about nucleotide 421 to 504, from about nucleotide 421 to 507, from about nucleotide 421 to 510, from about nucleotide 418 to 498, from about nucleotide 418 to 501, from about nucleotide 418 to 504, from about nucleotide 418 to 507, from about nucleotide 418 to 510, from about nucleotide 403 to 498, from about nucleotide 403 to 501, from about nucleotide 403 to 504, from about nucleotide 403 to 507, and from about nucleotide 403 to 510; (iv) a polynucleotide of (iii), wherein T is U; and (v) a polynucleotide comprising a sequence that is complementary to (iii) and (iv) above. A "polynucleotide" of the disclosure also includes those polynucleotides capable of hybridizing, under stringent hybridization conditions, to sequences of (iii)-(v), above. "Stringent hybridization conditions" refers to an overnight incubation at 42° C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C. It will be recognized that a polynucleotide of the disclosure, may be operably linked to a second heterologous polynucleotide such as a promoter or a heterologous sequence encoding a desired peptide or polypeptide sequence.

Any of various art-known methods for protein purification can be used to isolate the peptides of the disclosure. For example, preparative chromatographic separations and immunological separations (such as those employing monoclonal or polyclonal antibodies) can be used. Carrier peptides can facilitate isolation of fusion proteins that include the peptides of the disclosure. Purification tags can be operably linked to a cathelicidin functional fragment of the disclosure. For example, glutathione-S-transferase (GST) allows purification with a glutathione agarose affinity column. When either Protein A or the ZZ domain from *Staphylococcus aureus* is used as the tag, purification can be accomplished in a single step using an IgG-sepharose affinity column. The pOprF-peptide, which is the N-terminal half of the *P. aeruginosa* outer membrane protein F, can readily be purified because it is the prominent protein species in outer membrane preparations. If desired, the fusion peptides can be purified using reagents that are specifically reactive with (e.g., specifically bind) the cathelicidin functional fragment of the fusion peptide. For example, monoclonal or polyclonal antibodies that specifically bind the cathelicidin functional fragment can be used in conventional purification methods. Techniques for producing such antibodies are well known in the art.

A fusion construct comprising a peptide or polypeptide linked to a cathelicidin functional fragment of the disclosure can be linked at either the amino or carboxy terminus of the peptide. Typically, the polypeptide that is linked to the cathelicidin functional fragment is sufficiently anionic or cationic such that the charge associated with the cathelicidin functional fragment is overcome and the resulting fusion peptide has a net charge that is neutral or negative. The peptide or polypeptide linked to a peptide of the disclosure can correspond in sequence to a naturally-occurring protein or can be entirely artificial in design. Functionally, the polypeptide linked to a cathelicidin functional fragment (the "carrier polypeptide") may help stabilize the cathelicidin functional fragment and protect it from proteases, although the carrier polypeptide need not be shown to serve such a purpose. Similarly, the carrier polypeptide may facilitate transport of the fusion peptide. Examples of carrier polypeptides that can be utilized include anionic pre-pro peptides and anionic outer membrane peptides. Examples of carrier polypeptides include glutathione-S-transferase (GST), protein A of *Staphylococcus aureus*, two synthetic IgG-binding domains (ZZ) of protein A, outer membrane protein F of *Pseudomonas aeruginosa*, and the like. The disclosure is not limited to the use of these polypeptides; others suitable carrier polypeptides are known to those skilled in the art. In another aspect, a linker moiety comprising a protease cleavage site may be operably linked to a cathelicidin functional fragment or variant of the disclosure. For example, the linker may be operable between two domains of a fusion protein (e.g., a fusion protein comprising a cathelicidin functional fragment and a carrier polypeptide). Because protease cleavage recognition sequences generally are only a few amino acids in length, the linker moiety can include the recognition sequence within flexible spacer amino acid sequences, such as GGGGS (SEQ ID NO:12). For example, a linker moiety including a cleavage recognition sequence for Adenovirus endopeptidase could have the sequence GGGGGGSMFG GAKKRSGGGG GG (SEQ ID NO:29). If desired, the spacer DNA sequence can encode a protein recognition site for cleavage of the carrier polypeptide from the cathelicidin functional fragment. Examples of such spacer DNA sequences include, but are not limited to, protease cleavage sequences, such as that for Factor Xa protease, the methionine, tryptophan and glutamic acid codon sequences, and the pre-pro defensin sequence. Factor Xa is used for proteolytic cleavage at the Factor Xa protease cleavage sequence, while chemical cleavage by cyanogen bromide treatment releases the peptide at the methionine or related codons. In addition, the fused product can be cleaved by insertion of a codon for tryptophan (cleavable by o-iodosobenzoic acid) or glutamic acid (cleavable by *Staphylococcus* protease). Insertion of such spacer digonucleotides is not a requirement for the production of cathelicidin functional fragments, such oligonucleotide can enhance the stability of the fusion polypeptide.

In one aspect of the invention, carbonate and/or peptides of the disclosure are contacted with a subject to promote/stimulate host cell defence mechanisms by, for example, stimulating epithelia to release cytokines to mount a more effective cell-mediated immune response. For example, as demonstrated in FIGS. 1-9 bicarbonate promotes LL-37 activity. In addition, FIGS. 15-16 shows the effect of LL-37 and functional fragments on inflammatory cell recruitment and cytokine production.

The disclosure also provides a method for inhibiting the growth of a bacterium by contacting the bacterium with an inhibiting effective amount of a cathelicidin functional fragment of the disclosure. The term "contacting" refers to exposing the bacterium to a cathelicidin functional fragment peptide so that the peptide can inhibit, kill, or lyse bacteria. Contacting of an organism with a cathelicidin functional fragment of the disclosure can occur in vitro, for example, by adding the peptide to a bacterial culture to test for susceptibility of the bacteria to the peptide, or contacting a bacterially contaminated surface with the peptide. Alternatively, contacting can occur in vivo, for example by administering the peptide to a subject afflicted with a bacterial infection or susceptible to infection. In vivo contacting includes both parenteral as well as topical. "Inhibiting" or "inhibiting effective amount" refers to the amount of peptide that is sufficient to cause, for example, a bacteriostatic or bactericidal effect. Bacteria that can be affected by the peptides of the disclosure include both gram-negative and gram-positive bacteria. For example, bacteria that can be affected include *Staphylococcus aureus, Streptococcus pyogenes* (group A), *Streptococcus* sp. (viridans group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and *Branhamella catarrhalis*; Gram-positive bacilli such as *Bacillus anthracis, Bacillus subtilis, P. acne Corynebacterium diphtheriae* and *Corynebacterium* species which are diptheroids (aerobic and anerobic), *Listeria monocytogenes, Clostridium tetani, Clostridium difficile, Escherichia coli, Enterobacter* species, *Proteus mirabilis* and other sp., *Pseudomonas aeruginosa, Klebsiella pneumoniae, Salmonella, Shigella, Serratia*, and *Campylobacter jejuni*. Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, born infections, fascitis, bronchitis, and a variety of abscesses, nosocomial infections, and opportunistic infections. The method for inhibiting the growth of bacteria can also include contacting the bacterium with the peptide in combination with one or more antibiotics.

Fungal organisms may also be affected by the cathelicidin functional fragments of the disclosure and include dermatophytes (e.g., *Microsporum canis* and other *Microsporum* sp.; and *Trichophyton* sp. such as *T. rubrum*, and *T. mentagrophytes*), yeasts (e.g., *Candida albicans, C. Tropicalis,* or other *Candida* species), *Saccharomyces cerevisiae, Torulopsis glabrata, Epidermophyton floccosum, Malassezia furfur (Pityropsporon orbiculare,* or *P. ovale), Cryptococcus neoformans, Aspergillus fumigatus, Aspergillus nidulans,* and other *Aspergillus* sp., *Zygomycetes* (e.g., *Rhizopus, Mucor), Paracoccidioides brasiliensis, Blastomyces dermatitides, Histoplasma capsulatum, Coccidioides immitis,* and *Sporothrix schenckii*.

A peptide(s) of the disclosure can be administered to any host, including a human or non-human animal, in an amount effective to inhibit growth of a bacterium, virus, and/or fungus. Thus, the peptides are useful as antimicrobial agents, antiviral agents, and/or antifungal agents.

Any of a variety of art-known methods can be used to administer a polypeptide or peptide to a subject. For example, the polypeptide or peptide of the disclosure can be administered parenterally by injection or by gradual infusion over time. The peptide can be administered intravenously, intraperitoneally, intramuscularly, subcutaneously, intracavity, or transdermally.

In another aspect, a cathelicidin functional fragment of the disclosure may be formulated for topical administration (e.g., as a lotion, cream, spray, gel, or ointment). Such topical formulations are useful in treating or inhibiting microbial, fungal, and/or viral presence or infections on the eye, skin, and mucous membranes such as mouth, vagina and the like. Examples of formulations in the market place include topical lotions, creams, soaps, wipes, and the like. It may be formulated into liposomes to reduce toxicity or increase bioavailability. Other methods for delivery of the polypeptide or peptide include oral methods that entail encapsulation of the polypeptide or peptide in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a polypeptide or peptide of the disclosure include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, cheating agents, inert gases and the like also can be included.

The disclosure provides a method for inhibiting a topical bacterial, viral and/or fungal-associated disorder by contacting or administering a therapeutically effective amount of a polypeptide or peptide of the disclosure to a subject who has, or is at risk of having, such a disorder. The term "inhibiting" means preventing or ameliorating a sign or symptoms of a disorder (e.g., a rash, sore, and the like). Examples of disease signs that can be ameliorated include an increase in a subject's blood level of TNF, fever, hypotension, neutropenia, leukopenia, thrombocytopenia, disseminated intravascular coagulation, adult respiratory distress syndrome, shock, and organ failure. Examples of subjects who can be treated in the disclosure include those at risk for, or those suffering from, a toxemia, such as endotoxemia resulting from a gram-negative bacterial infection, venom poisoning, or hepatic failure. Other examples include subjects having a dermatitis as well as those having skin infections or injuries subject to infection with gram-positive or gram-negative bacteria, a virus, or a fungus. Examples of candidate subjects include those suffering from infection by *E. coli, Hemophilus influenza* B, *Neisseria meningitides, staphylococci,* or *pneumococci*. Other patients include those suffering from gunshot wounds, renal or hepatic failure, trauma, burns, immunocompromising infections (e.g., HIV infections), hematopoietic neoplasias, multiple myeloma, Castleman's disease or cardiac myxoma. Those skilled in the art of medicine can readily employ conventional criteria to identify appropriate subjects for treatment in accordance with the disclosure.

The term "therapeutically effective amount" as used herein for treatment of a subject afflicted with a disease or disorder means an amount of cathelicidin functional fragment sufficient to ameliorate a sign or symptom of the disease or disorder. For example, a therapeutically effective amount can be measured as the amount sufficient to decrease a subject's symptoms of dermatitis or rash by measuring the frequency of severity of skin sores. Typically, the subject is treated with an amount of cathelicidin functional fragment sufficient to reduce a symptom of a disease or disorder by at least 50%, 90% or 100%. Generally, the optimal dosage of the polypeptide or peptide will depend upon the disorder and factors such as the weight of the subject, the type of bacteria, virus or fungal infection, the weight, sex, and degree of symptoms. Nonetheless, suitable dosages can readily be determined by one skilled in the art. Typically, a suitable dosage is 0.5 to 40 mg peptide/kg body weight, e.g., 1 to 8 mg peptide/kg body weight.

A "viral killing amount" of antiviral is an amount sufficient to achieve a virus-killing blood concentration or a viral-killing surface concentration in or on the patient or subject receiving the treatment. In accordance with its conventional definition, an "antiviral agent," as used herein, is a chemical or biologic substance that inhibits the growth of, spread of, or kills viral particles.

If desired, a suitable therapy regime can combine administration of a polypeptide or peptide of the disclosure with one or more additional therapeutic agents (e.g., an inhibitor of TNF, an antibiotic, and the like). The peptide(s), other therapeutic agents, and/or antibiotic(s) can be administered, simultaneously, but may also be administered sequentially. Suitable antibiotics include aminoglycosides (e.g., gentamicin), beta-lactams (e.g., penicillins and cephalosporins), quinolones (e.g., ciprofloxacin), and novobiocin. In addition, the N-terminal cathelin-like fragment of SEQ ID NO:6 has antibacterial activity. Accordingly, a combination of the N-terminal fragment of SEQ ID NO:6 comprising the cathelin-like domain (e.g., SEQ ID NO:6 from about amino acid 31 to amino acid 131) and the C-terminal domain comprising a cathelicidin functional fragment can be co-administered or administered sequentially. Generally, the antibiotic is administered in a bactericidal, antiviral and/or antifungal amount. The peptide provides for a method of increasing antibiotic activity by permeabilizing the bacterial outer membrane and combinations involving peptide and a sub-inhibitory amount (e.g., an amount lower than the bactericidal amount) of antibiotic can be administered. Typically, the cathelicidin functional fragment and antibiotic are administered within 48 hours of each other (e.g., 2-8 hours, or may be administered simultaneously). A "bactericidal amount" is an amount sufficient to achieve a bacteria-killing blood concentration in the subject receiving the treatment. In accordance with its conventional definition, an "antibiotic," as used herein, is a chemical substance that, in dilute solutions, inhibits the growth of, or kills microorganisms. Also encompassed by this term are synthetic antibiotics (e.g., analogs) known in the art.

The polypeptides or peptides of the disclosure can be used, for example, as preservatives or sterilants of materials susceptible to microbial or viral contamination. For example, the peptides can be used as preservatives in processed foods (e.g., to inhibit organisms such as *Salmonella, Yersinia,* and *Shigella*). If desired, the peptides can be used in combination with antibacterial food additives, such as lysozymes. The peptides of the disclosure can also be used as a topical agent, for example, to inhibit *Pseudomonas* or *Streptococcus* or kill odor-producing microbes (e.g., *Micrococci*). The optimal amount of a cathelicidin functional fragment of the disclosure for any given application can be readily determined by one of skill in the art.

The cathelicidin functional fragments of the disclosure are also useful in promoting would repair and tissue regeneration. Matrix metalloproteinases (MMPs) are inflammatory enzymes that degrade proteins in various tissues. Recent scientific research has shown elevated levels of proteases (e.g., MMPs) in chronic wound exudate, the fluid that bathes the wound bed. These excess proteases cause degradation of important extracellular matrix proteins and inactivation of vital growth factors that are essential in the wound healing process. This may contribute to a sub-optimal healing environment resulting in delayed wound healing.

The cathelicidin functional fragments of the disclosure can be used to treat damaged tissue, such as wounds (in particular chronic wounds), more effectively. As demonstrated herein, the cathelicidin functional fragments of the disclosure are effective protease inhibitors. The cathelicidin functional fragments of the disclosure are capable of inhibiting the action of specific proteins that are upregulated in a wound environment wherein those proteins have an adverse effect in the wound environment. Typically the adverse effect is a deleterious effect on wound healing. Hence, the cathelicidin functional fragments of the disclosure can be used to inhibit the deleterious effects of proteases that are upregulated in a wound environment. Simultaneously, the cathelicidin functional fragments of the disclosure also are capable of serving as antibacterial agents that reduce the risk of infection at a wound site by inhibiting proteases produced by pathogens in the wound site.

Intracellular mature virions (IMV) of vaccinia have a double layer membrane of endoplasmic reticulum derived membrane cisternae. As the IMV migrates through an infected cell the virion acquires a double layer outer envelope consisting of a cellular cisternae known as a wrapping membrane and become intracellular enveloped virions. Egress from the cell is accompanied by fusion of the outermost layer with the plasma membrane yielding a three layer outer membrane on extra-cellular enveloped virions (EEV). Both the IMV and EEV forms are infectious with the EEV being most efficient in cell entry. The disclosure demonstrates that cathelicidin functional fragments, related homologues, and variants thereof, are effective at disrupting the IMV and EEV of the virions thus being useful as antiviral agents.

The disclosure includes the use of cathelicidin functional fragments for treatment of viral skin disease, especially for the treatment of vaccinia and small pox infection. As the molecules are proteins, they are most well suited for topical application. However, peptidomimetics and other protein analogs with more favorable pharmacokinetic and pharmacodynamic properties can be developed for use with other routes of administration including, but not limited to, oral and parenteral. The compounds can be incorporated into appropriate delivery devices dependent upon the route of administration and other considerations well known to those skilled in the art. Additionally as cathelicidin functional fragments are peptides, the coding sequence could be delivered to the site of interest using any gene transfer protocol to allow for expression of the gene product.

The cathelicidin functional fragments can be used in conjunction with vaccination to ameliorate or prevent eczema vaccination or after vaccination for the treatment of skin conditions. The cathelicidins can also be used for infections developed due to infection from other sources.

The disclosure provides cathelicidin functional fragments which have antiviral activity. The cathelicidin functional fragments are useful for inhibiting viral infection or spread, as well reducing the effects of viral infection. One or more cathelicidin functional fragment peptides can be used, for example, as an antiviral agent in topical lotions as well as in other pharmaceuticals including soaps and wipes. A cathelicidin functional peptide fragment of the disclosure can be used alone or in combination with conventional antiviral agents and can be used as an adjunct therapy.

Resolution of infection and protection against re-infection with viruses depends on cooperation between innate and adaptive immune processes. These processes include antiviral proteins, complement activation, macrophages, NK, numerous cytokines, cytotoxic T cells, specific antibodies and $\gamma/\delta$ T cells. In addition to the alteration in the skin barrier in atopic dermatitis (AD), alterations in cellular immunity have been described in this disease. These alterations are possible candidate mechanisms for the serious consequences of herpes viruses and vaccinia virus in this skin disease. Goodyear et al. had previously observed increased quantities of HSV when cultured on skin explants obtained from patients with AD and psoriasis compared to skin from normal individuals (Clin. Exp. Dermatol. 21:185, 1996). These experimental conditions were performed in the absence of many of these defense mechanisms. Eczema vaccinatum is a complication of smallpox vaccination seen within ten days after virus inoculation during primary immunization, also suggesting an important role for local, innate immune responses in restricting vaccinia viral replication.

The effect of cathelicidin functional fragments on vaccinia virus have not been reported. The mechanism of action for these peptides is hypothesized to involve disruption of the microbial membrane and/or the penetration of the microbial membranes to interfere with intracellular functions. Keratinocytes are primary producers of cathelicidin and LL-37 in the skin following injury or an inflammatory skin response. The disclosure demonstrates the effect of cathelicidins functional fragments on vaccinia virus replication in vitro.

Eczema Vaccinatum (EV) is one of the major complications of small pox vaccination and occurs in patients with a history of atopic dermatitis (AD), a Th2-mediated skin disease. Recently it was found that AD skin is deficient in its ability to express certain endogenous antimicrobial peptides, also known as cathelicidins, such as LL-37 (Ong et al., NEJM 2002; 347:1151-60). This group of patients is known to be much more susceptible to serious complications of infection with vaccinia and related viruses. Vaccinia virus is used for small pox vaccination.

The term "purified" or "substantially purified" as used herein refers to a peptide that is substantially free of other proteins, lipids, and nucleic acids (e.g., cellular components with which an in vivo-produced peptide would naturally be associated). Typically, the peptide is at least 70%, 80%, 90%, or more pure by weight.

The disclosure also provides a method for inhibiting the spread or infection of a virus by contacting the virus or a surface upon which a virus may be present with an inhibiting effective amount of a cathelicidin functional fragment peptide of the disclosure. The term "contacting" refers to exposing the virus to a cationic antiviral peptide so that the peptide can inhibit the spread of infectivity of a virus or kill the virus itself. For example, by adding a cathelicidin functional fragment to a culture comprising a virus (e.g., vaccinia virus) one can measure the susceptibility of a culture to the infectivity of a virus in the presence and absence of a cathelicidin functional fragment. Alternatively, contacting can occur in vivo, for example, by administering a cathelicidin functional fragment to a subject that is susceptible to or afflicted with a viral infection. The administration includes topical as well as parenteral. "Inhibiting" or "inhibiting effective amount" refers to the amount of a peptide that is sufficient to cause a viral inhibition or kill a virus. Examples of viruses that can be inhibited include herpesviridae (herpes simplex virus (HSV), varicella-zoster virus), vaccinia virus, Pappiloma virus and other viruses causing skin diseases. The method for inhibiting the viral infection can also include the contacting of a virus with a cathelicidin functional fragment alone or in combination with one or more other antiviral agents.

The cathelicidin functional fragments are also useful as a broad-spectrum antimicrobials suitable for tackling the growing problem of antibiotic-resistant bacteria strains, and for treating and/or preventing outbreaks of infectious diseases, including diseases caused by bioterrorism agents like anthrax, plague, cholera, gastroenteritis, multidrug-resistant tuberculosis (MDR TB). The cathelicidin functional fragments, kits, and carbonate preparations of the disclosure can be used therapeutically and prophylactically for biodefense against new bioattacks. For example, the disclosure provides kits containing formulations comprising a cathelicidin functional fragment of the disclosure and/or carbonate formulations. The kits can be provided, for example, to a population subject to bioterrorist attacks (e.g., the military). The carbonate preparations can be applied/administered either before (prophylactic) during or after exposure to a pathogenic viral organism, bacteria, fungus, or mutant strains thereof, to induce a subject's natural LL-37/cathelicidin activity. Alternatively, the subject can apply/administer a cathelicidin functional fragment either alone or in combination with a formulation comprising a carbonate agent.

A cathelicidin functional fragment(s) of the disclosure can be administered to any host, including a human or non-human animal, in an amount effective to inhibit growth of a virus, bacterial or fungus.

In another aspect, the invention provides methods and compositions useful to treat microbial, viral, and/or fungal infections comprising contacting or administering to a subject at risk of or having an infection a carbonate composition that modulates the activity of LL-37 or cathelicidin functional fragments.

Any of a variety of art-known methods can be used to administer a cathelicidin functional fragment and/or a carbonate composition to a subject. For example, a composition of the disclosure can be administered parenterally by injection or by gradual infusion over time. The peptide can be administered intravenously, intraperitoneally, intramuscularly, subcutaneously, intracavity, or transdermally. In another aspect, a composition of the disclosure may be formulated for topical administration (e.g., as a lotion, cream, spray, gel, or ointment). Examples of formulations in the market place include topical lotions, creams, soaps, wipes, and the like. It may be formulated into liposomes to reduce toxicity or increase bioavailability. Other methods for delivery of the peptide include oral methods that entail encapsulation of the peptide in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a peptide of the disclosure include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antiviral agents, anti-oxidants, cheating agents, inert gases and the like also can be included.

The disclosure provides a method for inhibiting viral infection and spread of such viruses as herpesviridae (herpes simplex virus (HSV), varicella-zoster virus), vaccinia virus, Pappiloma virus and other viruses causing skin diseases, as well as diseases and disorders associated with atopic dermatitis by administering a therapeutically effective amount of a cathelicidin functional fragment of the disclosure to a subject who has, or is at risk of having, such an infection or disorder. The term "inhibiting" means preventing or ameliorating infectivity of a virus or a sign or symptoms of a disorder (e.g., atopic dermatitis). Examples of disease signs that can be ameliorated include skin sores and lesions associated with herpesviridae (herpes simplex virus (HSV), varicella-zoster virus), vaccinia virus, Pappiloma virus and other viruses causing skin infection such as those seen in atopic dermatitis. Examples of patients who can be treated in the disclosure include those at risk for, or those suffering from, a viral infection, such as those resulting from Herpesviridae (herpes simplex virus (HSV), varicella-zoster virus), vaccinia virus, Pappiloma virus and other viruses causing skin diseases. Those skilled in the art of medicine can readily employ conventional criteria to identify appropriate subjects for treatment in accordance with the disclosure.

The cathelicidin functional fragment of the disclosure can be used, for example, as preservatives or sterillants of materials susceptible to viral contamination. For example, the peptides can be used as preservatives in processed foods, as spray disinfectants commonly used in the household or clinical environment. The optimal amount of a cationic peptide of the disclosure for any given application can be readily determined by one of skill in the art.

In another aspect, the disclosure provides knockout non-human animals that are useful to screen potential antiviral and antibacterial cathelicidin functional fragments and agents useful for treating such diseases and disorders as atopic dermatitis.

As a model to study the potential in vivo significance of LL-37 deficiency, CRAMP Cnlp knockout mice known to lack expression of CRAMP, a close murine ortholog of catheliocidin human LL-37, were developed and used. Importantly these mice generated a significantly greater number of pox skin lesions than seen in wild type isogenic control mice. The two mice that did not generate pox skin lesions died within two days of septic shock following smallpox vaccination.

These in vitro and in vivo observations suggest that the increased susceptibility of atopic dermatitis patients to eczema vaccinatum may be due to a deficiency of cathelicidin. Such knockout mice are effective models to test the therapeutic effects of cathelicidin functional fragments.

The following examples are intended to illustrate but not limit the disclosure. While they are typical of those that might be used, other procedures known to those skilled in the art may alternatively be used.

EXAMPLES

Materials and Methods

Sweat collection and processing. Sweat was collected on paper tissues (Kimwipes, Kimberly-Clark, GA) from healthy volunteers after exercise. After collection, 20 ml of sweat was centrifuged at 2000 g for 15 min. at 4° C., filtered through a 0.20 ml filter (Acrodisc syringe filter, 0.2 mm, low protein binding, Fisher scientific, Tustin, Calif.), and frozen at –80° C. For some experiments sweat was lyophilized to dryness, then suspended in 400 µl of distilled water (DW: cell culture grade, endotoxin free, GibcoBRL, Grand island, NY). For analysis of LL37 processing by sweat, 1.6 nmol of LL-37 synthetic peptide was incubated in 50 ml of sweat for 0, 1, 6, 24 hrs at 37° C. or 4° C. In some experiments proteinase inhibitors including; mixed protease inhibitor cocktail (1tab/10ml, Roche, Indianapolis, Ind.), 100 mg/ml Bestatin, 10 mg/ml E-64, 10 mg/ml Aprotinin, (Sigma, St Louis, Mo.); 100 mM AEBSF, 100 mM Neutrophil elastase inhibitor (NEI) or 100 mM leukocyte elastase inhibitor (LEI)(Calbiochem, San Diego, Calif.) were added during incubation. After incubation, 2 ml was assayed by radial diffusion assay to determine antibacterial activity. For analysis by HPLC 32 nmoles LL-37 was incubated in 100 ul. To control for potential contamination from paper tissues, parallel processing was done on tissues soaked in phosphate-buffered saline (PBS:137 mM NaCl, 2.7 mM KCL, 4.3 mM Na2HPO4-H20, 1.4 mM KH2PO4, pH 7.4). No antimicrobial activity was detectable in these preparations. Protein concentrations were evaluated by BCA assay (protein assay reagent, Pierce, Rockford, Ill.) or Bradford protein assay (Bio-Rad, Hercules, Calif.) according to manufacture's instructions. Human tissue and blood collection was approved by the UCSD Human Research Protection Program.

Peptide synthesis. Dermcidin, LL-37, RK-31, KS-30, and KR-20 peptides were commercially prepared by Synpep Corporation, Dublin, Oreg. Peptide amino acid sequences were LLGDFFRKSKEKIGKEFKRIVQRIKDFLRNLVPRTES (LL-37)(SEQ ID NO:32), RKSKEKIGKEFKRIVQRIKDFLRNLVPRTES (RK-31)(SEQ ID NO:27), KSKEKIGKEFKRIVQRIKDFLRNLVPRTES (KS-30) (SEQ ID NO:22), KRIVQRIKDFLRNLVPRTES (KR-20) (SEQ ID NO:17), SSLLEKGLDGAKKAVGGLGKLGK-DAVEDLESVGKGAVHDVKDVLDSV) (dermcidin)(SEQ ID NO:33). All 5 synthetic peptides were purified by HPLC and identity confirmed by mass spectrometry.

HPLC chromatography. Peptide separation was performed using an AKTA purification system (Amersham Pharmacia Biotech, Piscataway, N.J.) on a Sephasil peptide C18 column (12 mm, ST 4.6/250, Amersham Pharmacia Biotech, Piscataway, N.J.). Concentrated human sweat, or LL-37 incubated in sweat, was separated by reversed phase (RP-HPLC) following column equilibration in 0.1% TFA at a flow rate of 0.5 ml/ml and eluted using gradients of 0-35% and 35-60% acetonitrile for 16 min, 67 min, or 0-60% acetonitrile for 120 min. Column effluent was monitored at 214, 230, and 280 nm. All collected fractions (1 ml) were lyophilized and suspended in 10 ml of DW for antimicrobial radial diffusion assay.

Western and Immunoblot analysis. Fractions purified by HPLC as described above were evaluated by quantitative dot-blot and Western Blot. 2 µl of each fraction was compared to a standard curve of synthetic LL37 peptide applied onto PVDF membrane (Immobilon-P, Millipore, Mass.). Antibody used was rabbit anti-LL-37 polyclonal antibody derived and affinity purified against the entire LL-37 peptide. For immunoblot, membranes were blocked (0.1% TTBS: 5% nonfat milk in 0.1% Tween 20/tris buffered saline (TBS: 150 mM NaCl, 10 mM Tris Base, pH 7.4)) for 60 min at room temperature, and then rabbit anti LL37 polyclonal antibody (1:5000 in blocking solution) was incubated with the membrane overnight at 4° C. After washing 3× with 0.1% TTBS, horseradish peroxidase labeled goat anti rabbit antibody (1:5000 in the blocking solution, (DAKO, CA) was incubated with the membrane for 60 min, room temperature. After washing the membrane again with 0.1% TTBS, the membrane was immersed in ECL solution (Western Lightning Chemiluminescence Reagents Plus, New Lifescience Products, Boston, Mass.) for 60 sec then exposed to X-ray film (Kodak). For, Western-blot analysis, sweat samples (10 µl) were separated by 16.5% tristricine/peptide gel (BIO-RAD, Hercules, Calif.), and then transferred on to a PVDF membrane (Immobilon-P, Millipore, Mass.). For positive control, 5 pmol LL-37 synthetic peptide was applied.

Mass spectrometry and Protein sequence analysis. Mass spectrometry was performed by Center for Mass Spectrometry, The Scripps Research Institute (La Jolla, Calif.). MALDI-MS spectra were obtained with a Voyager DE-RP MALDI-TOF mass spectrometer (PerSeptive Biosystems, Framingham, Mass.) equipped with a nitrogen laser (337 nm, 3-ns pulse). Spectra were collected in reflector mode. The accelerating voltage in the ion source was 20 kV. Data were acquired with a transient recorder with 2-ns resolution. The matrix used in this work was -cyano-4-hydroxycinnamic acid dissolved in water/acetonitrile (1:1, v/v) to give a saturated solution at room temperature. To prepare the sample for analysis, 1 µl of the peptide solution (containing 1-10 pmol of protein in 0.1% trifluoroacetic acid) was added to 1 µl of the matrix solution and applied to a stainless steel sample plate. The mixture was then allowed to air dry on the sample plate before being introduced into the mass spectrometer. Each spectrum was produced by accumulating data using 128 laser pulses. Mass assignments were assigned with an accuracy of approximately ±0.1% (±1 Da/1000 Da). Protein sequence analysis for target HPLC fractions was performed by Division of Biology Protein Sequencer Facility, University of California, San Diego.

The amino acid sequencing was performed on an Applied Biosystems Procise Model 494 sequencer using the "pulsed-liquid" program supplied by the manufacture.

Antimicrobial assays. For screening of antimicrobial activity of HPLC fractions, radial diffusion assay was used. Lyophilized HPLC fractions were dissolved in DW (GibcoBRL, Grand Island, N.Y.), and tested against Staphylococcus aureus mprF. Thin plates (1 mm) of 1% agarose in 0.5% tryptone containing approximately $1 \times 10^6$ cells/ml of S. aureus mprF were used. 1 mm wells were punched in the plates and 2 ml of samples dissolved in tissue culture grade sterile water were loaded in each well.

As a positive control, synthetic LL-37 was applied to separate wells. After incubation at 37° C. overnight, the inhibition zones were recorded by CCD camera and diameters measured. To evaluate antimicrobial activity against wild-type *S. aureus* (clinical isolate), and enteroinvasive *E. coli* O29, both radial diffusion and solution killing assays were done. Radial diffusion assays were done as described for *S. aureus* mprF. Solution killing was done in 10% TSB in 10 mM PB (TSB=30 gm/L Tryptic Soy Broth, Sigma, St Louis Mo.; 20×PB=27.6 g/L NaH2PO4-H2O, 53.65 g/L Na2HPO4-7H2O, pH 7.4). Bacteria in log-phase growth were suspended to $1 \times 10^6$ cells/ml, peptide added and incubated at 37° C. for 2 hr. Bacteria were then plated on TSB agar (TSB, Bactoagar 13 g/L, Becton Dickinson, Sparks Md.) for direct colony count and determination of CFU.

Activity against Group A *Streptococcus* (NZ131) was done only in solution assay as described. To evaluate antimicrobial activity in high salt conditions, solution assay was done in 10% TSB/10 mM PBS with several salt concentrations (concentration of NaCl; 10, 50, 100, 150, 300, 500 mM). Action against the *C. albicans* was determined in Dixon medium (0.6% Peptone, 4% Malt Extract, 1% Glucose, 0.1% Ox Bile, 1% Tween-80) in sterile 96-well microtiter plates (Corning Inc., Corning, N.Y.) at a final volume of 50 ml. The assay mixtures contained $1\text{-}2.5 \times 10^4$ PFU/ml freshly grown *Candida*, 20% Dixon medium, 0.6 mM phosphate buffer pH 7, and 16 mg/ml chloramphenicol. Microtiter plates were incubated at 37° C. for 24 h with peptides, then plated on Dixon agar to determine the MFC (minimum fungicide concentration).

Hemolysis Assay. Hemolytic activity was determined on human whole blood. Freshly obtained whole blood was washed 3× in PBS and resuspended in PBS at its original volume containing peptides at indicated concentrations. Samples were incubated at 37° C. for 1.5 to 3 h, and hemolysis determined by centrifuging at 300 g and measurement of the absorbance of the supernatant at 578 nm. Hemolytic activity of each peptide was expressed as the percentage of total hemoglobin released compared to that released by incubating with 0.1% Triton X-100.

Measurement of IL-8 release from keratinocytes Normal human keratinocytes (NHK) were cultured in EpiLife cell medium (Cascade Biologics, Portland, Oreg.) containing 0.06 mM Ca2+, 1× EpiLife-defined growth supplement (EDGS), 50 U/ml penicillin and 50 mg/ml streptomycin (In-vitrogen, Carlsbad, Calif.). Keratinocytes were seeded in a 96-well plate and grown to confluence under standard tissue culture conditions. Cells were incubated with 3 mM or 10 mM LL-37 or LL37-derived peptides (e.g., cathelicidin functional fragments) for 8 hours at 37° C. Supernatants were collected and stored at −20° C. overnight. IL-8 ELISA Assay was performed according to the manufacturer's instructions (BD OptEIA, Pharmingen, San Diego, Calif.). Supernatants were diluted 1:10 for assay. Simultaneously, LDH assays (Roche, Indianapolis, Ind.) were used to assess the cytotoxicity of peptides to keratinocytes. LDH release following peptide exposure was compared to release induced by 1% Triton X100.

Results

Figure 10:
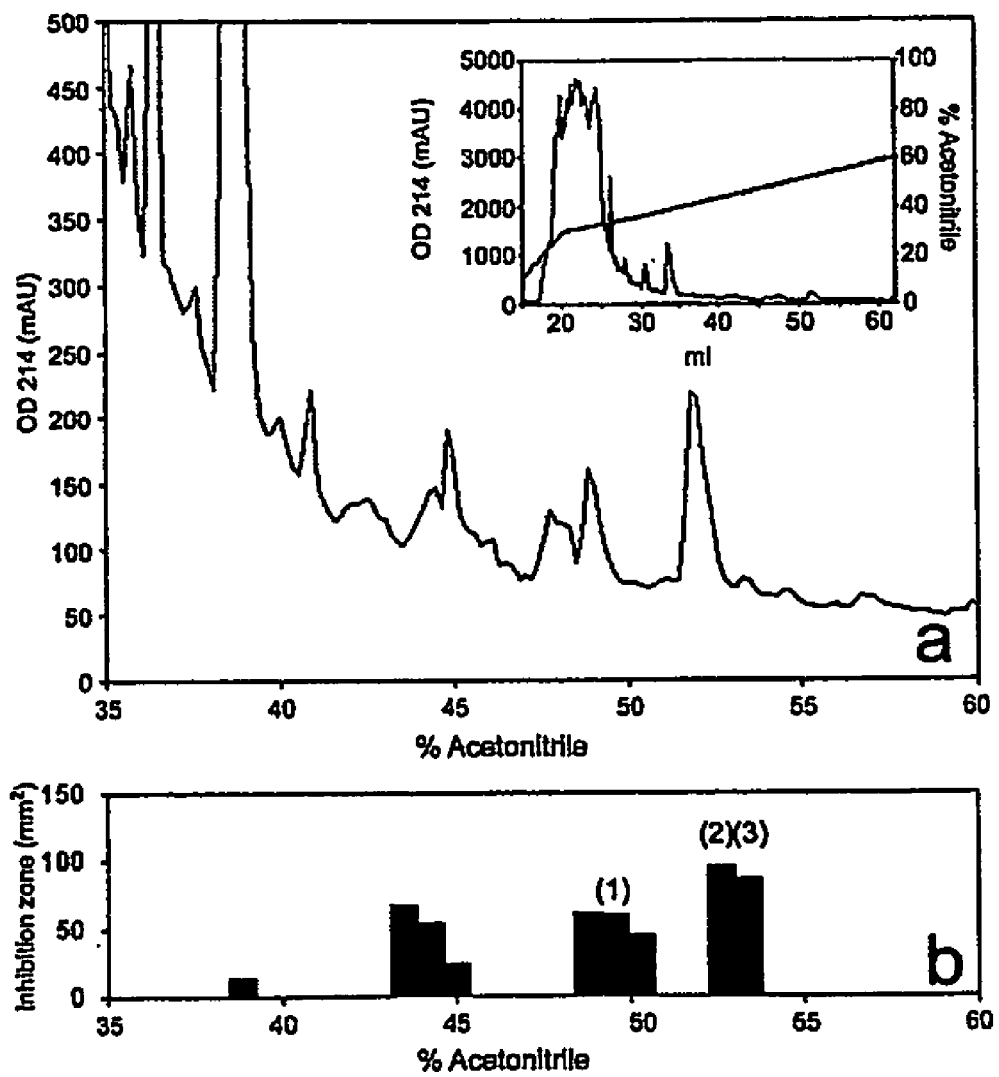
FIG. 10A-B shows soluble antimicrobial activity on human skin. Human sweat was concentrated 50× and separated by HPLC on C18. a) Absorbance profile at 214 nm for eluted material from 35% to 60% acetonitrile, inset: complete absorbance profile of eluted materials. b) Ability of material eluted in FIG. 1a to inhibit growth of *S. aureus* mprF is shown as diameter of zone of *S. aureus* mprF inhibition. Several antimicrobial fractions were detected. Mass spectrometry identified previously described antimicrobials; fractions labeled (1) and (3) are dermcidin and DCD-1L respectively (MW 4701, MW 4818, respectively) confirmed by N-terminal sequencing ((1): SSLLEKGLDGA (SEQ ID NO:30), (3)

To identify antimicrobial activity present at the skin surface, human sweat was collected from normal volunteers, concentrated, and separated by high performance liquid chromatography (HPLC). Fractions of the material eluted between 35-65% acetonitrile were individually evaluated for the ability to inhibit the growth of *S. aureus* mprF by radial diffusion assay (FIG. 10). Multiple distinct fractions were found to be active in this assay. Prior evaluations of human sweat have shown that the antimicrobial peptides LL-37 and dermcidin are produced by the eccrine apparatus and secreted into the topical soluble environment of sweat. As expected, these molecules were detectable in the sweat preparation shown in FIG. 10. The presence of LL-37 was confirmed by immunoblot analysis with antibody specific to LL-37 and by MALDI-TOF mass spectrometry. The dermcidin peptides, DCD and DCD-1L, were identified by MALDI-TOF mass spectrometry and N-terminal amino acid sequencing.

Immunoblot analysis with anti-LL-37 antibody of all fractions isolated by HPLC from the human sweat suggested that other molecules related to LL-37 may be present in fractions eluting between 43 and 48% acetonitrile. These fractions were associated with antimicrobial activity but not identifiable by MALDI-TOF mass spectrometry and N-terminal amino acid sequencing from the concentrated sweat preparations. Based on the immunoreactivity and elution profile we hypothesized that these antimicrobial molecules were alternative forms of LL-37 that were further processed in sweat to unique cathelicidin peptides. To test this, human sweat was freshly collected, sterilely filtered, then synthetic LL-37 added to a final concentration of 32 mM. The relative ability of this solution to inhibit the growth of *S. aureus* mprF was then evaluated. Following incubation at 37° C. in sweat, LL-37 increased the zone of inhibition and apparent antimicrobial activity (FIG. 11*a*). Incubation of LL-37 under identical conditions in PBS or distilled water did not affect activity. This increase in apparent antimicrobial activity did not occur at 4° C. and was inhibited by the addition of protease inhibitor cocktail, thus suggesting the gain in antimicrobial function was a consequence of an enzymatic process (FIG. 11*b*). Addition of specific inhibitors of potential processing enzymes demonstrated that the serine protease inhibitors AEBSF and Aprotinin were most effective in blocking the increase in antimicrobial activity generated by incubation of LL-37 in sweat (FIG. 11*c*).

Figure 13:
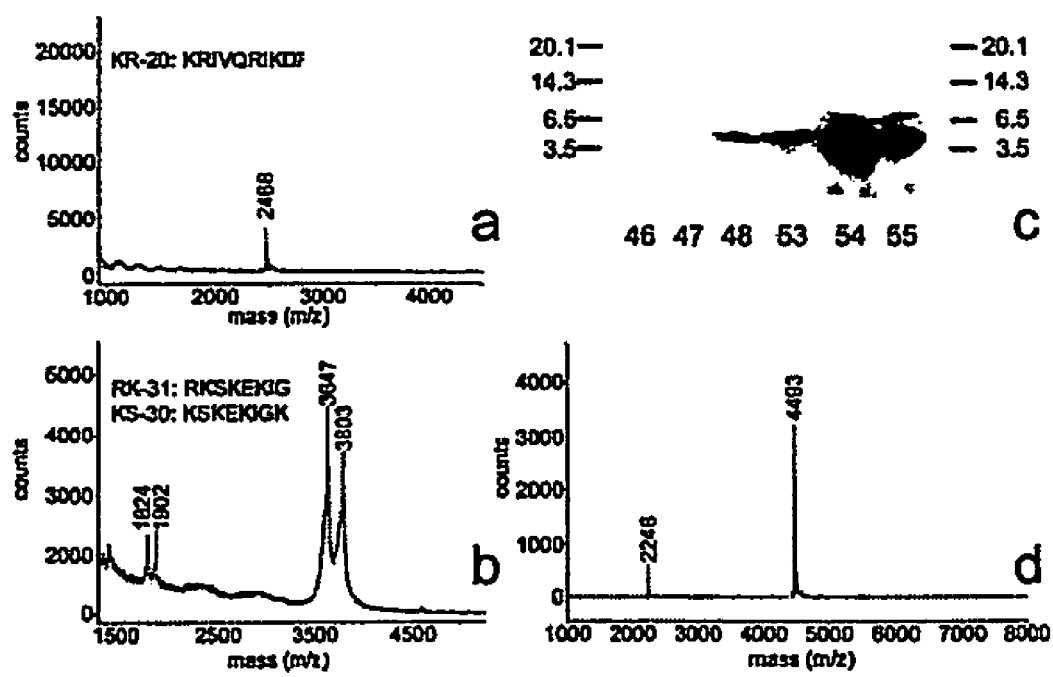

An increase in the relative ability of LL-37 to inhibit growth of *S. aureus* mprF suggested that the enzymatic processing of this peptide resulted in alternative forms with either increased direct antimicrobial activity or an ability to synergize with the parent peptide. To identify these processed forms of LL-37, synthetic peptide was incubated with the sterile sweat preparation and separated by HPLC after various periods of incubation (FIG. 12*a*). An increase in the relative abundance of several proteins was seen over time. Correlation of this profile with antimicrobial activity showed fractions eluding at 39% and 48% acetonitrile gained antimicrobial activity coincident with and increase in relative abundance of peptides eluting at these positions (FIG. 12*b*). A third major peak of antimicrobial activity seen between 53 and 56% acetonitrile showed a relative decrease in abundance as estimated by absorbance at 214 nm. MALDI-TOF mass spectrometry and N-terminal sequencing of the peptide eluding at 39% acetonitrile identified this as a 20 amino acid cathelicidin derivative, KR-20 (FIG. 13*a*). Similar analysis of peptides eluding at 48% acetonitrile identified two additional cathelicidin peptides RK-31 and KS-30 (FIG. 13*b*). Western blot analysis with antibody against LL-37 confirmed antigenic similarity of RK-31 and KS-30 to parent LL-37 (FIG. 13*c*). KR-20 was not detectable with this antibody. Material eluting at 55-56% acetonitrile and decreasing in abundance with incubation was identified as LL-37 by both Western blot and Mass spec analysis (FIGS. 13*c* and *d*).

The newly described human cathelicidin peptides KR-20, RK-31 and KS-30 eluded at positions corresponding to unidentified antimicrobial activity seen in crude sweat preparations partially purified in FIG. 10. The low relative abundance of these peptides, yet easily detectable antimicrobial activity suggested that these peptides might gain antimicrobial activity with processing when compared to LL-37. To compare the antimicrobial activity of these cathelicidins, purified synthetic peptides corresponding to LL-37, RK-31, KS-30 and KR-20 were assessed by both radial diffusion assay and solution assay against a variety of microbes (FIG. 14). RK-31 and KS-30 showed greatly increased action against wild-type *S. aureus* and *E. coli*. And all three new peptides showed increased fungicidal activity against *Candida albicans*. Furthermore, these peptides were synergistic, killing bacteria at lower concentrations when present together, (FIG. 14d), and maintained activity at increased salt conditions (FIGS. 14e,f). Hemolytic activity against human erythrocytes was minimal as seen by assay at a concentration 5 to 10 times greater than that required for antimicrobial activity (Table 2).

TABLE 2

Antimicrobial and hemolytic activity of human sweat peptides.

| | Radial Diffusion Assay (μm) | | | Liquid Assay (μm) | | |
|---|---|---|---|---|---|---|
| | S. aureus MprF | S. aureus (wt) | E. coli (O29) | GAS (NZ131) | C. albicans ATCC 14053 | % hemolysis |
| LL-37 | 32 | >64 | 64 | 8 | 20 | 9 |
| RK-31 | 8 | 16 | 8 | 8 | 4 | 6 |
| KS-30 | 8 | 16 | 8 | 4 | 2 | .23 |
| KR-20 | 16 | >64 | >64 | 4 | 10 | 0 |
| DCD | >64 | >64 | >64 | >64 | >32 | nd |

Radial diffusion assay results represent minimal inhibitory concentrations (MIC) determined for peptides against indicated bacteria. Liquid assay results represent minimal concentration required to kill Group A *Streptococcus* (GAS) or *Candida albicans*. Percent hemolysis is shown for peptides at the following concentrations: LL-37 and KR-20=100 μM; RK-31=44 μM; KS-30=88 μM. nd=not done.

However, despite gaining antimicrobial activity by processing to shorter forms of the cathelicidin peptide, hemolytic activity of these antimicrobials decreased relative to LL-37.

In addition to the function of antimicrobial peptides as natural antibiotics, many of these molecules have been associated with the ability to stimulate a variety of host responses. To determine if the secretion and processing of cathelicidin peptides at the surface of the skin could also stimulate a host inflammatory response, human keratinocytes were grown in culture and assayed for the release of IL-8 in response to these peptides. All peptide solutions were endotoxin free. LL-37 had a potent ability to stimulate IL-8 release from keratinocytes, but processing to the shorter form of these cathelicidins decreased the ability to stimulate IL-8 (FIG. 15). Cellular toxicity of these peptides was simultaneously evaluated by determination of the release of lactate dehydrogenase into keratinocyte culture medium. At a concentration of 3 mM none of the peptides evaluated significantly increased the permeability of keratinocyte membranes.

LL-37 was demonstrated to bind FPRL-1, induces neutrophil and mast cell chemotaxis (see, e.g., FIG. 16). LL-37 blocks pro-inflammatory chemokine release from dendritic cells, but induces pro-inflammatory release from keratinocytes. CRAMP has similar effect in mouse dendritic cells (FIG. 17) and inhibits antigen presentation in vitro (FIG. 18A-C). This effect is dissociated from cathelicidin functional fragments.

Figure 19:
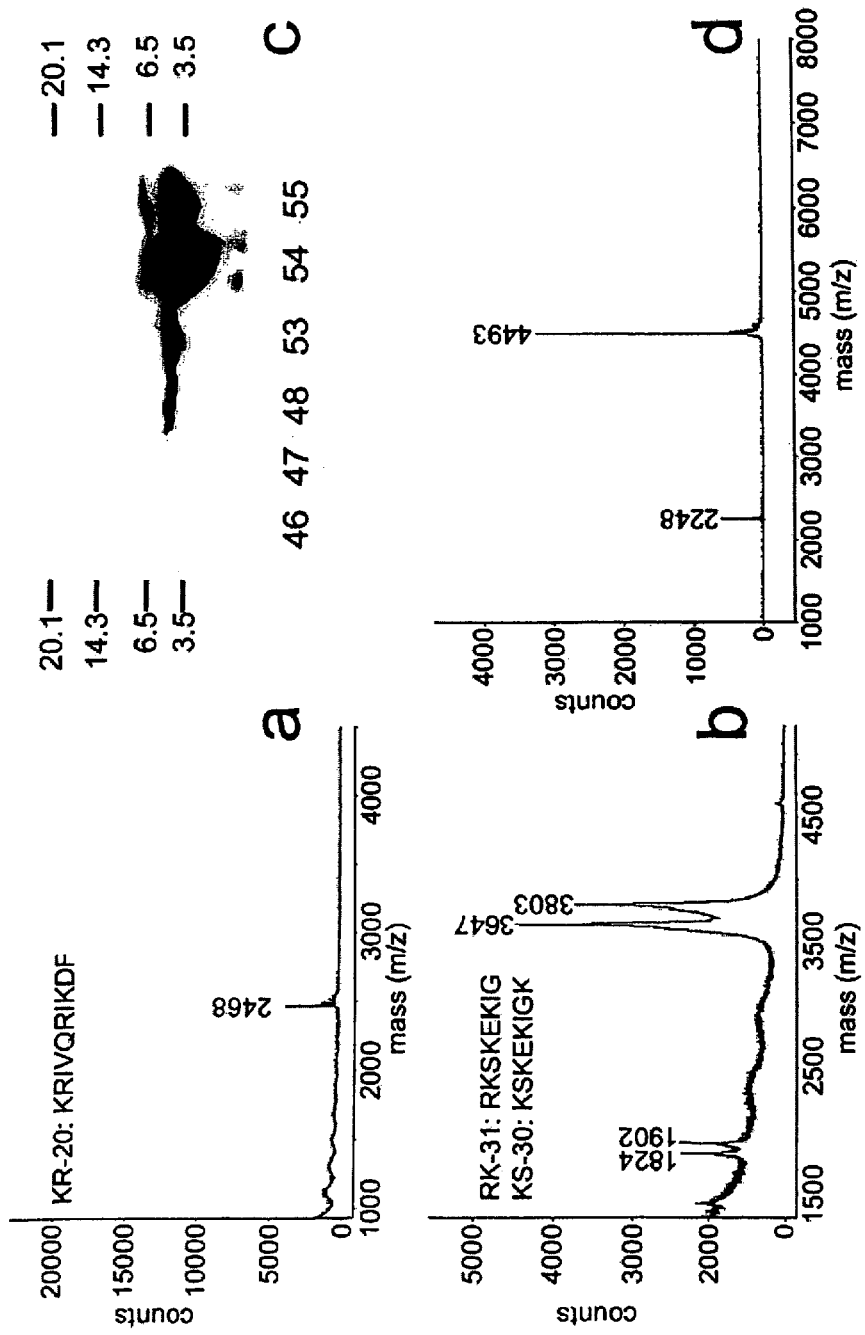

FIG. 19A-C shows the identification of cathelicidin function fragments on the normal skin surface by HPLC. FIG. 20 shows a schematic of cathelicidin processing on the normal skin surface.

A number of embodiments of the invention have been described. Nevertheless, it will be understood that various modifications may be made without departing from the spirit and scope of the invention. Accordingly, other embodiments are within the scope of the following claims.

What is claimed is:

1. A method for inhibiting the spread and/or reducing the risk of infection of a virus comprising contacting a virus with an inhibiting effective amount of a cathelicidin functional fragment, wherein the cathelicidin functional fragment consists of 16-20 or 26-30 amino acids in length; and contains the sequence $X_1X_2X_3X_4X_5X_6IKX_7FX_8X_9X_{10}LX_{11}P$ (SEQ ID NO:1), wherein $X_1$, $X_2$, and $X_6$ are individually K or R; wherein $X_3$ is I or K; wherein $X_4$ is V or G; wherein $X_5$ is Q or R; wherein $X_7$, $X_9$, $X_{10}$, and $X_{11}$ are each individually any amino acid; wherein $X_8$ is L or F and wherein the polypeptide comprises antimicrobial and/or antiviral activity.

2. The method of claim 1, wherein the peptide comprises a sequence selected from the group consisting of:

| | |
|---|---|
| (a) KRIVQRIKDFLRNLVP; | (SEQ ID NO:13) |
| (b) KRIVQRIKDFLRNLVPR; | (SEQ ID NO:14) |
| (c) KRIVQRIKDFLRNLVPRT; | (SEQ ID NO:15) |
| (d) KRIVQRIKDFLRNLVPRTE; and | (SEQ ID NO:16) |
| (e) KRIVQRIKDFLRNLVPRTES. | (SEQ ID NO:17) |

3. The method of claim 1, wherein the peptide comprises a sequence selected from the group consisting of:

| | |
|---|---|
| (a) KSKEKIGKEFKRIVQRIKDFLRNLVP; | (SEQ ID NO:18) |
| (b) KSKEKIGKEFKRIVQRIKDFLRNLVPR; | (SEQ ID NO:19) |
| (c) KSKEKIGKEFKRIVQRIKDFLRNLVPRT; | (SEQ ID NO:20) |
| (d) KSKEKIGKEFKRIVQRIKDFLRNLVPRTE; and | (SEQ ID NO:21) |
| (e) KSKEKIGKEFKRIVQRIKDFLRNLVPRTES. | (SEQ ID NO:22) |

4. A method for inhibiting the spread and/or reducing the risk of infection of a virus comprising contacting a virus with an inhibiting effective amount of a cathelicidin functional fragment, wherein the fragment consists of a sequence selected form the group consisting of:

| | |
|---|---|
| (a) RKSKEKIGKEFKRIVQRIKDFLRNLVP; | (SEQ ID NO:23) |
| (b) RKSKEKIGKEFKRIVQRIKDFLRNLVPR; | (SEQ ID NO:24) |
| (c) RKSKEKIGKEFKRIVQRIKDFLRNLVPRT; | (SEQ ID NO:25) |
| (d) RKSKEKIGKEFKRIVQRIKDFLRNLVPRTE; | (SEQ ID NO:26) |
| (e) RKSKEKIGKEFKRIVQRIKDFLRNLVPRTES. | (SEQ ID NO:27) |
| (f) LGDFFRKSKEKIGKEFKRIVQRIKDFL-RNLVPRTES. | (SEQ ID NO: 28) |

5. The method of claim 1, wherein the virus is selected from a pox virus, a herpes virus, vaccinia virus, and pappiloma virus.

6. The method of claim 1, wherein the contacting is in vivo.

7. The method of claim 6, wherein the contacting is in vivo is by topical administration.

8. A method for treating atopic dermatitis comprising contacting a subject having or suspected of having atopic dermatitis with an inhibiting effective amount of a cathelicidin functional fragment, wherein the cathelicidin functional fragment consists of 16-20or 26-30 amino acids in length; and contains the sequence $X_1X_2X_3X_4X_5X_6IKX_7FX_8X_9X_{10}LX_{11}P$ (SEQ ID NO: 1), wherein $X_1$, $X_2$, and $X_6$ are individually K or R; wherein $X_3$ is I or K; wherein $X_4$ is V or G; wherein $X_5$ is Q or R; wherein $X_7$, $X_9$, $X_{10}$, and $X_{11}$ are each individually any amino acid; wherein $X_8$ is L or F and wherein the polypeptide comprises antimicrobial and/or antiviral activity.

9. The method of claim 8, wherein the peptide comprises a sequence selected from the group consisting of:

| | |
|---|---|
| (a) KRIVQRIKDFLRNLVP; | (SEQ ID NO:13) |
| (b) KRIVQRIKDFLRNLVPR; | (SEQ ID NO:14) |
| (c) KRIVQRIKDFLRNLVPRT; | (SEQ ID NO:15) |

-continued (d) KRIVQRIKDFLRNLVPRTE; (SEQ ID NO:16)
and (e) KRIVQRIKDFLRNLVPRTES. (SEQ ID NO:17)

10. The method of claim 8, wherein the peptide comprises a sequence selected from the group consisting of:

(a) KSKEKIGKEFKRIVQRIKDFLRNLVP; (SEQ ID NO:18)

(b) KSKEKIGKEFKRIVQRIKDFLRNLVPR; (SEQ ID NO:19)

(c) KSKEKIGKEFKRIVQRIKDFLRNLVPRT; (SEQ ID NO:20)

(d) KSKEKIGKEFKRIVQRIKDFLRNLVPRTE; (SEQ ID NO:21)
and (e) KSKEKIGKEFKRIVQRIKDFLRNLVPRTES. (SEQ ID NO:22)

11. A method for treating atopic dermatitis comprising contacting a subject having or suspected of having atopic dermatitis with an inhibiting effective amount of a cathelicidin functional fragment, wherein the fragment consists of a sequence selected from the group consisting of:

(a) RKSKEKIGKEFKRIVQRIKDFLRNLVP; (SEQ ID NO:23)

(b) RKSKEKIGKEFKRIVQRIKDFLRNLVPR; (SEQ ID NO:24)

(c) RKSKEKIGKEFKRIVQRIKDFLRNLVPRT; (SEQ ID NO:25)

(d) RKSKEKIGKEFKRIVQRIKDFLRNLVPRTE; (SEQ ID NO:26)

(e) RKSKEKIGKEFKRIVQRIKDFLRNLVPRTES. (SEQ ID NO:27)

(f) LGDFFRKSKEKIGKEFKRIVQRIKDFL-RNLVPRTES. (SEQ ID NO: 28)

12. The method of claim 8 or 11, wherein the subject also is inflected with a viral infection, wherein the virus is selected from a pox virus, a herpes virus, vaccinia virus, and pappiloma virus.

13. The method of claim 8 or 11, wherein the contacting is in vivo.

14. The method of claim 13, wherein the contacting in vivo is by topical administration.

* * * * *

UNITED STATES PATENT AND TRADEMARK OFFICE
CERTIFICATE OF CORRECTION

| | | |
|---|---|---|
| PATENT NO. | : 7,718,618 B2 | Page 1 of 1 |
| APPLICATION NO. | : 10/575552 | |
| DATED | : May 18, 2010 | |
| INVENTOR(S) | : Richard L. Gallo, Masamoto Murakami and Donald Y. M. Leung | |

It is certified that error appears in the above-identified patent and that said Letters Patent is hereby corrected as shown below:

Column 1, lines 16 to 18, should read as follows:
--This invention was made with government support under Grant Nos. AR41256 and AI052453 awarded by the National Institutes of Health. The government has certain rights in the invention.--

Signed and Sealed this

Nineteenth Day of April, 2011

David J. Kappos
*Director of the United States Patent and Trademark Office*